United States Patent
Peters et al.

(10) Patent No.: US 7,238,774 B2
(45) Date of Patent: Jul. 3, 2007

(54) STATINE DERIVATIVES FOR THE TREATMENT OF ALZHEIMER'S DISEASE III

(75) Inventors: Stefan Peters, Biberach (DE); Klaus Fuchs, Schemmerhofen (DE); Christian Eickmeier, Mittelbiberach (DE); Werner Stransky, Gau-Algesheim (DE); Cornelia Dorner-Ciossek, Ravensburg (DE); Sandra Handschuh, Warthausen (DE); Herbert Nar, Ochsenhausen (DE); Klaus Klinder, Oggelshausen (DE); Marcus Kostka, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/268,197

(22) Filed: Nov. 7, 2005

(65) Prior Publication Data

US 2006/0100158 A1    May 11, 2006

(30) Foreign Application Priority Data

Nov. 10, 2004   (EP) ................... 04026671

(51) Int. Cl.
*A61K 38/03* (2006.01)
(52) U.S. Cl. .................................... 530/300
(58) Field of Classification Search ............. None
See application file for complete search history.

(56) References Cited

U.S. PATENT DOCUMENTS

2003/0125257 A1   7/2003   Brockhaus et al.
2006/0160747 A1   7/2006   Peters

FOREIGN PATENT DOCUMENTS

| EP | 0040435 | 11/1981 |
| EP | 0312157 | 4/1989 |
| EP | 0316907 | 5/1989 |
| JP | 61 275256 A | 12/1986 |
| WO | 9210509 | 6/1992 |
| WO | WO 92/13545 A | 8/1992 |
| WO | WO 00/77030 A | 12/2000 |
| WO | WO2004/101603 A1 | 11/2004 |

OTHER PUBLICATIONS

Hu et al. "Design and Synthesis of Statine-Containing BACE Inhibitors," Bioorg. Med. Chem. Let., 2003, 13, 4335-9.*
Mourier, Nicolas, et al: "Peptide-nucleoside conjugates: Synthesis and antii-HIV activities" Nucleosides and Nucleotides, vol. 14, No. 6, 1995, pp. 1393-1402.
Shiosaki, K. et al: "Potent and selective inhiitors of an aspartyl protease-like endothelin converting enzyme identified in rat lung" Journal of Medicinal Chemistry, American Chemical Society. Washington, US, vol. 36 No. 4, Feb. 19, 1993, pp. 468-478.
Zuo, Z. et al: "Molecular docking and 3D-QSAR studies on the binding mechanism of statine-based peptidomimetics with beta-secretase" Bioorganic & Medicinal Chemistry, Elsevier Science Ltd, GB, vol. 13, No. 6, Mar. 15, 2005; pp. 2121-2131; abstract; table 1.
Kuzmic, P., et al: "Long Range Electrostatic Effects in Pepsion Catalysis" Tetrahedron, Elsevier Science Publishers, Amsterdam, NL, vol. 47, No. 14/15, 1991 pp. 2519-2534.
Hu, Jingdan; et al: "Design and Synthesis od Statine-Containing Bace Inhibitors", Bioorganic ans Medical Chemistry Letters 13, (2003) 43335-4339, XP 002304453.

* cited by examiner

*Primary Examiner*—Cecilia J. Tsang
*Assistant Examiner*—Christina Marchetti Bradley
(74) *Attorney, Agent, or Firm*—Michael P. Morris; Mary-Ellen M. Devlin; Timothy X. Witkowski

(57) ABSTRACT

The invention relates to a compound of the formula (I)

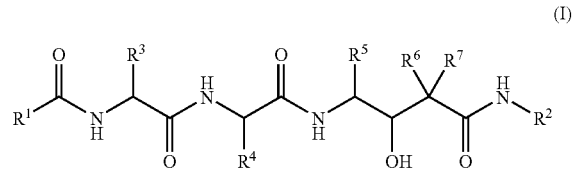

wherein $R^1$, $R^2$, $R^3$, $R^4$, $R^5$, $R^6$, $R^7$ and $R^8$ are defined as in the specification and claims and to its use for treating or preventing Alzheimer's disease and other similar diseases.

18 Claims, No Drawings

STATINE DERIVATIVES FOR THE TREATMENT OF ALZHEIMER'S DISEASE III

BACKGROUND OF THE INVENTION

1. Technical Field

The invention relates to novel statine derivatives and to their use for treating or preventing Alzheimer's disease and other similar diseases.

2. Background Information

Alzheimer's disease (AD) is a progressive degenerative disease of the brain primarily associated with aging. Clinical presentation of AD is characterized by loss of memory, cognition, reasoning, judgement, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD.

Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurodegenerative disorders. Beta-amyloid is a defining feature of AD, now believed to be a causative precursor or factor in the development of disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39–42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp2, am Memapsin2. See, for example, Sindha et. al., 1999, Nature 402: 537–554 and published PCT application WO00/17369.

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, Neuron 6: 487–498. Release of A beta from neuronal cells grown in culture and the presence of A beta in cerebrospinal fluid (CSF) of both normal individuals and AD patients has been demonstrated. See, for example, Seubert et al., 1992, Nature 359: 325–327.

It has been proposed that A beta peptide accumulates as a result of APP processing by beta-secretase, thus inhibition of this enzyme's activity is desirable for the treatment of AD, see for example Vassar, R. 2002, Adv. Drug Deliv. Rev. 54, 1589–1602 In vivo processing of APP at the beta-secretase cleavage site is thought to be a rate-limiting step in A beta production, and is thus a therapeutic target for the treatment of AD. See for example, Sabbagh, M., et al., 1997, Alz. Dis. Rev. 3,1–19.

BACE1 knockout mice fail to produce A beta, and present a normal phenotype. When crossed with transgenic mice that overexpress APP, the progeny show reduced amounts of A beta in brain extracts as compared with control animals (Luo et. al., 2001 Nature Neuroscience 4: 231–232). This evidence further supports the proposal that inhibition of beta-secretase activity and reduction of A beta in the brain provides a therapeutic method for the treatment of AD and other beta amyloid disorders.

The International patent application WO00/47618 identifies the beta-secretase enzyme and methods of its use. This publication also discloses oligopeptide inhibitors that bind the enzyme's active site and are useful in affinity column purification of the enzyme. In addition, WO00/77030 discloses tetrapeptide inhibitors of beta-secretase activity that are based on a statine molecule.

Various pharmaceutical agents have been proposed for the treatment of Alzheimer's disease but without any real success. U.S. Pat. No. 5,175,281 discloses aminosteroids as being useful for treating Alzheimer's disease. U.S. Pat. No. 5,502,187 discloses bicyclic heterocyclic amines as being useful for treating Alzheimer's disease.

EP 652 009 A1 discloses inhibitors of aspartyl protease which inhibit beta amyloid peptide production in cell culture and in vivo. The compounds which inhibit intracellular beta-amyloid peptide production are useful in treating Alzheimer's disease.

WO00/69262 discloses a new beta-secretase and its use in assays to screen for potential drug candidates against Alzheimer's disease.

WO01/00663 discloses memapsin 2 (human beta-secretase) as well as catalytically active recombinant enzyme. In addition, a method of identifying inhibitors of memapsin 2, as well as two inhibitors are disclosed. Both inhibitors that are disclosed are peptides.

WO01/00665 discloses inhibitors of memapsin 2 that are useful in treating Alzheimer's disease.

At present there are no effective treatments for halting, preventing, or reversing the progression of Alzheimer's disease. Therefore, there is an urgent need for pharmaceutical agents with sufficient plasma and/or brain stability capable of slowing the progression of Alzheimer's disease and/or preventing it in the first place.

Compounds that are effective inhibitors of beta-secretase, that inhibit beta secretase-mediated cleavage of APP, that are effective inhibitors of A beta production, and/or are effective to reduce amyloid beta deposits or plaques, are needed for the treatment and prevention of disease characterized by amyloid beta deposits or plaques, such as AD.

BRIEF SUMMARY OF THE INVENTION

Surprisingly, it has been found that the statine derivatives of formula (I) of the present invention have superior properties, like inhibition of beta secretase-mediated cleavage of APP. Thus the invention relates in a first embodiment to compounds of group 1 according to formula (I)

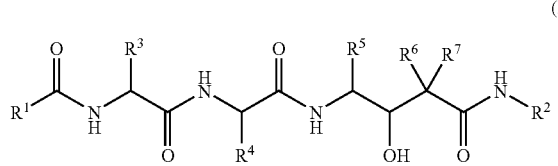

wherein
R$^1$ represents
a) a carboxy-C$_{1-6}$-alkyl-,
b) a C$_{1-6}$-alkyl-O—CO—C$_{1-6}$-alkyl-,
c) a C$_{3-8}$-cycloalkyl- or C$_{3-8}$-cycloalkyl-C$_{1-3}$-alkyl-,
d) a heterocyclyl-,
e) a aryl-, or a aryl-C$_{1-3}$-alkyl-, or
f) a heteroaryl-group
  wherein each of said groups may be optionally substituted by one or more substituents independently selected from the group consisting of C$_{1-6}$-alkyl-, aryl-CO—, C$_{1-6}$-alkyl-O—, C$_{1-6}$-alkyl-O—CO—, C$_{1-6}$-alkyl-CO—, C$_{1-6}$-alkyl-CO—NR$^8$—, halogen-, carboxy-, hydroxy-, nitro-, oxo- or (R$^8$)$_2$N—SO$_2$-groups,
R$^2$ represents
(a) a C$_{1-6}$-alkyl- or C$_{2-6}$-alkenyl-group,
  optionally substituted by one or more substituents independently selected from the group consisting of heteroaryl-, phenyl-, C$_{3-8}$-cycloalkyl- or heterocyclyl-groups,
    wherein the phenyl group may be optionally substituted by one or more substituents independently selected from the group consisting of C$_{1-3}$-alkyl-groups which may be optionally substituted with a hydroxyl-group, cyano-, C$_{1-3}$-alkynyl-, halogen, hydroxy-, carboxy-, nitro-, (R$^8$)$_2$N—CO—, (R$^8$)$_2$N— or C$_{1-3}$-alkyl-N(R$^8$)C(O)N(R$^8$)-groups, or
(b) a bicyclic carbocyclic ring, optionally substituted by one or more substituents independently selected from the group consisting of C$_{1-3}$-alkyl-, halogen, hydroxy-, carboxy-, nitro-, (R$^8$)$_2$N—CO— or (R$^8$)$_2$N-groups,
R$^3$ represents a C$_{1-6}$-alkyl-, C$_{1-6}$-alkylthio-C$_{1-3}$-alkyl-, C$_{2-6}$-alkenyl, C$_{2-6}$-alkinyl or a C$_{3-8}$-cycloalkyl-C$_{1-3}$-alkyl-group,
  optionally substituted by one or more substituents independently selected from the group consisting of fluor or cyano-,
R$^4$ represents a C$_{1-6}$-alkyl-, C$_{2-6}$-alkenyl-, C$_{3-8}$-cycloalkyl-C$_{1-3}$-alkyl-, aryl-, aryl-C$_{1-3}$-alkyl- or a heteroaryl-C$_{1-3}$-alkyl-group,
  wherein each of said groups may be optionally substituted by one or more substituents independently selected from the group consisting of C$_{1-6}$-alkyl-, C$_{1-6}$-alkyl-O—, (R$^8$)$_2$N—CO—, aryl-C$_{1-3}$-alkyl-O— or hydroxy-groups,
R$^5$ represents a C$_{1-6}$-alkyl-, C$_{3-8}$-cycloalkyl-C$_{1-3}$-alkyl- or a aryl-C$_{1-3}$-alkyl-group,
  wherein each of said groups may be optionally substituted by one or more substituents independently selected from C$_{1-6}$-alkyl-S— or a halogen atom, wherein the halogen atom is preferably a fluor atom,
R$^6$ and R$^7$ each independently represent hydrogen or a halogen atom, preferably hydrogen or a fluor atom, more preferably hydrogen,
R$^8$ represents hydrogen or a C$_{1-6}$-alkyl-group, preferably a hydrogen,
or pharmaceutically acceptable tautomers, enantiomers, diastereomers, salts or solvates thereof.

Furthermore, the invention relates to a pharmaceutical composition comprising a compound of formula (I) or a pharmaceutically acceptable salt or solvate thereof and a pharmaceutically acceptable carrier or diluent.

Another aspect of the present invention is the use of a compound of formula (I) or a pharmaceutically acceptable salt or solvate thereof in the manufacture of a medicamentation for use in treating a patient who has, or in preventing a patient from getting, a disease or condition selected from Alzheimer's disease, diffuse Lewy body type of Alzheimer's disease, Down's syndrome, MCI ("Mild Cognitive Impairment"), Heriditary Cerebral Hemorrhage with Amyloidosis of the Dutch-Type, Cerebral Amyloid Angiopathy, Traumatic Brain Injury, Stroke, Dementia, Parkinson's Disease and Parkinson's Syndrome, or central or peripheral amyloid diseases.

Furthermore the invention relates to a method for inhibiting β-secretase activity, comprising exposing said β-secretase to an effective inhibitory amount of a compound of formula (I).

The present invention provides compounds, compositions, kits, and methods for inhibiting beta-secretase-mediated cleavage of amyloid precursor protein (APP).

More particularly, the compounds, compositions, and methods of the invention are effective to inhibit the production of A beta peptide and to treat or prevent any human or veterinary disease or condition associated with a pathological form of A beta peptide.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD.

The compounds of the invention possess beta-secretase inhibitory activity.

The inhibitory activities of the compounds of the invention are readily demonstrated, for example, using one or more of the assays described herein or known in the art.

DETAILED DESCRIPTION OF THE INVENTION

The present invention relates to statine derivatives of formula (I) that are useful in treating and preventing Alzheimer's disease.

Some expressions used hereinbefore and below to describe the compounds according to the invention will now be defined more fully.

The term alkyl in the present invention denotes, unless otherwise stated, a unbranched or branched hydrocarbon group having 1 to 6 carbon atoms, preferably 1 to 4 carbon atoms, most preferably 1 to 3 carbon atoms, especially 1 or 2 carbon atoms. Examples are methyl, ethyl, propyl, butyl, pentyl, hexyl, etc. Unless otherwise stated the above terms propyl, butyl, pentyl, hexyl also include all the possible isomeric forms like n-propyl, isopropyl, n-butyl, iso-butyl, tert-butyl, n-pentyl, iso-pentyl, neo-pentyl, tert-pentyl, n-hexyl, iso-hexyl, etc. In some cases common abbreviations are also used to denote the above mentioned alkyl groups, such as Me for methyl, Et for ethyl etc.

The term haloalkyl (including those which are part of other groups, especially haloalkoxy) denotes, unless otherwise stated, branched or unbranched alkyl groups with 1 to 8 carbon atoms, preferably 1 to 6 carbon atoms, more preferably 1 to 5 carbon atoms, which are substituted by at least one halogen atom, particularly fluorine atom. Fluorinated groups of the formula

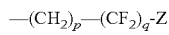
—$(CH_2)_p$—$(CF_2)_q$-Z wherein
p denotes 0 or an integer from 1 to 3,
q denotes an integer from 1 to 3, and
Z denotes hydrogen or fluorine, are preferred.

Examples include: trifluoromethyl, trifluoromethoxy, difluoromethoxy, perfluoroethyl, perfluoropropyl, 2,2,2-trifluoroethyl, 2,2,2-trifluoroethoxy, 1,1,1-trifluoroprop-2-yl, etc.

The term halogen generally denotes fluorine, chlorine, bromine or iodine particularly F, Cl and Br.

The term alkenyl denotes, unless otherwise stated, branched or unbranched hydrocarbon groups having from 2 to 6 carbon atoms, preferably 2 to 4 carbon atoms, most preferably 2 or 3 carbon atoms and from one to three double bonds and includes, for example, ethenyl, propenyl, allyl, 1-butenyl, 1-pentenyl, 1-hexenyl and the like.

The term alkynyl denotes, unless otherwise stated, branched or unbranched hydrocarbon groups having from 2 to 6 carbon atoms, preferably 2 to 4 carbon atoms, most preferably 2 or 3 carbon atoms and one or two triple bonds and includes ethynyl, propynyl, propargyl, butynyl, pentynyl and the like.

The term cycloalkyl (including those which are part of other groups, especially cycloalkyl-alkyl- or cycloalkoxy-) denotes, unless otherwise stated, saturated carbocyclic groups with 3 to 12 carbon atoms. The cycloalkyl can be monocyclic, or a polycyclic fused system. Preferably the cycloalkyl group is monocyclic with 3 to 8 carbon atoms, most preferably 3, 5 or 6 carbon atoms, especially 3 or 6 carbon atoms. Examples are: cyclopropyl, cyclobutyl, cyclopentyl, cyclohexyl, cycloheptyl, cyclooctyl etc. Most preferred is cyclopropyl and cyclohexyl.

The term bicyclic carbocyclic ring, unless otherwise stated, denotes a saturated or unsaturated but not aromatic 8–10 membered fused bicyclic ring whose ring forming atoms are solely carbon atoms. Typical bicyclic carbocyclic rings include but are not limited to

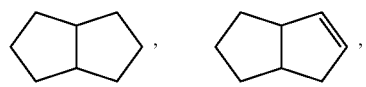

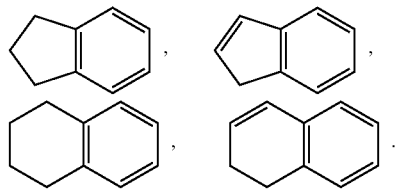

Preferred bicyclic carbocyclic rings are indanyl- and 1,2,3,4-tetrahydro-naphthalene.

The term aryl group, unless otherwise stated, denotes an aromatic carbocyclic group having a single ring (e.g., phenyl), multiple rings (e.g., biphenyl), or multiple condensed aromatic rings (e.g. naphthyl, anthryl). Examples are: phenyl, biphenyl, 1-naphthyl, 2-naphthyl, anthracenyl, phenanthrenyl. A particularly preferred meaning of "aryl" is phenyl.

The term heteroaryl group, unless otherwise stated, denotes one or more aromatic or unsaturated ring systems of 5-, 6-, or 7-membered rings which includes fused ring systems of 9–11 atoms containing 1, 2, 3, or 4 heteroatoms selected from nitrogen, oxygen, or sulfur. The term heteroaryl includes also the partially hydrogenated aromatic heterocyclic ring systems. Examples are: thiophenyl, pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyridin-2-yl-N-oxide, pyridin-3-yl-N-oxide, pyridin-4-yl-N-oxide, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide, benzo[1,3]dioxol.

The term heteroaryl group embraces also heteroaryl groups containing an oxidized nitrogen atom in the ring (N-oxides). For example, the term pyridin-4-yl N-oxide designates the following group,

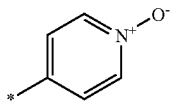

the term pyridin-3-yl N-oxide designates the following group,

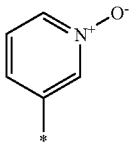

and the term pyridin-2-yl N-oxide designates the following group

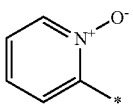

Particularly preferred heteroaryl groups are thienyl, pyridinyl, pyridin-2-yl N-oxide, pyridin-3-yl N-oxide, pyridin-4-yl N-oxide-, 6-oxo-1,6-dihydropyridazin-3-yl, pyrazinyl and indolyl.

The term heterocyclyl group, unless otherwise stated, denotes one or more saturated carbocyclic ring systems of 3-, 4-, 5-, 6-, or 7-membered rings which includes fused ring systems of 9–11 atoms containing at least 1, 2, 3, or 4 heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, morpholinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, azepanyl, diazepanyl, tetrahydrothienyl S-oxide, tetrahydrothienyl S,S-dioxide and homothiomorpholinyl S-oxide. Especially preferred heterocyclyl groups are piperidinyl and morpholinyl.

Terms such as cycloalkyl-alkyl-, heterocyclyl-alkyl-, aryl-alkyl-, heteroaryl-alkyl- refer to alkyl groups, as defined above, which are substituted with a cycloalkyl, heterocyclyl, aryl or heteroaryl group. Examples of aryl-alkyl-groups are benzyl or 2-phenylethyl. Examples for cycloalkyl-alkyl-groups are cyclopropylmethyl-, cyclohexylmethyl or cyclopentylethyl.

Many of the terms given above may be used repeatedly in the definition of a formula or group and in each case have one of the meanings given above, independently of one another.

The term "optionally substituted" used in this application indicates that the group thus designated is either unsubstituted or mono- or polysubstituted by the substituents specified. If the group in question is polysubstituted, the substituents may be identical or different.

The compounds of the present invention contain asymmetric carbon atoms and may be present in the form of one of the possible isomers or as a mixture thereof, e.g. depending on the number, absolute and relative configurations of the asymmetric carbon atoms as pure isomers, such as antipodes and/or diastereoisomers, or as isomeric mixtures, such as enantiomeric mixtures, e.g. racemates, diastereoisomeric mixtures or racemic mixtures; the invention relates to both the pure isomers and all the possible isomeric mixtures, and is to be understood as such hereinbefore and hereinafter, even if stereochemical details are not specifically mentioned in each case.

The symbol "-" in general represents a bond between two atoms in a chain and the point of attachment of a group to the rest of the molecule as defined. For example, an aryl-$C_{1-3}$-alkyl-group indicates an arylalkyl-group (e.g. 2-phenylethyl-) wherein the phenyl group is attached to the ethyl group and the ethyl group is attached to the rest of the molecule. The numeration of the atoms of a substituent starts with the atom which is closest to the rest of the moelcule to which the substituent is attached.

For example, the term "3-carboxypropyl-group" represents the following substituent:

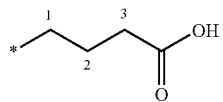

wherein the carboxy group is attached to the third carbon atom of the propyl group. The terms "1-methylpropyl-", "2,2-dimethylpropyl-" or "cyclopropylmethyl-" group represent the following groups:

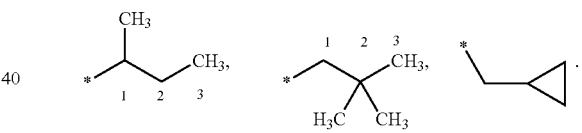

The asterisk is used in sub-formulas to indicate the bond which is connected to the rest of the molecule as defined.

In a preferred embodiment the present invention relates to compounds of group 1.a according to formula (I), wherein $R^1$ represents a group selected from a 3-carboxypropyl-, 3-methoxycarbonylpropyl-, 1-methyl-cyclohexyl-, 1-acetylpiperidin-3-yl-, 1-benzoylpiperidin-3-yl-, phenyl-, 3-carboxyphenyl-, 3-hydroxyphenyl-, 4-hydroxyphenyl-, 2-fluoro-4-hydroxyphenyl-, 3-fluoro-4-hydroxyphenyl-, 3-chloro-4-hydroxyphenyl-, 3,5-dichloro-4-hydroxyphenyl-, 3-acetylaminophenyl-, 3-acetylphenyl-, 4-methoxyphenyl-, 3-nitrophenyl-, 4-nitrophenyl-, 3-nitro-4-hydroxyphenyl-, 4-methoxycarbonylphenyl-, 3-methoxycarbonylphenyl-, 4-hydroxy-2,3,5,6-tetrafluorophenyl-, 4-sulfamoylphenyl-, 3-hydroxybenzyl-, 4-hydroxybenzyl-, 1-(4-hydroxyphenyl)-2-methylpropyl-, 5-hydroxypyrazin-2-yl-, 6-hydroxypyridin-3-yl-, 6-oxo-1,6-dihydropyridazin-3-yl-, pyridin-2-yl-, pyridin-3-yl-, pyridin-4-yl-, pyridin-2-yl N-oxide, pyridin-3-yl N-oxide or a pyridin-4-yl N-oxide group, and $R^2$, $R^3$, $R^4$, $R^5$, $R^6$, $R^7$ and $R^8$ are defined as for the compounds of group 1, or pharmaceutically acceptable tautomers, enantiomers, diastereomers, salts or solvates thereof.

In a further preferred embodiment the present invention relates to compounds of group 1.b according to formula (I), wherein R¹ represents a group selected from a 3-carboxypropyl-, pyridin-2-yl N-oxide, pyridin-3-yl N-oxide, pyridin-4-yl N-oxide or a phenyl-group,
wherein the phenyl group is substituted by one or more substituents independently selected from the group consisting of hydroxy groups, carboxy groups or halogen atoms, preferably fluor atoms and hydroxy groups, and R², R³, R⁴, R⁵, R⁶, R⁷ and R⁸ are defined as for the compounds of group 1, or pharmaceutically acceptable tautomers, enantiomers, diastereomers, salts or solvates thereof.

In a further preferred embodiment the present invention relates to compounds of group 1.c according to formula (I), wherein R¹ represents a group selected from a 3-carboxypropyl-, pyridin-4-yl N-oxide, 3-carboxyphenyl- or a 4-hydroxy-2,3,5,6-tetrafluorophenyl-group, and R², R³, R⁴, R⁵, R⁶, R⁷ and R⁸ are defined as for the compounds of group 1, or pharmaceutically acceptable tautomers, enantiomers, diastereomers, salts or solvates thereof.

In a further preferred embodiment the present invention relates to compounds of group 1.d according to formula (I), wherein R¹ represents a group selected from a 3-carboxypropyl- or a pyridin-4-yl N-oxide-group, and R², R³, R⁴, R⁵, R⁶, R⁷ and R⁸ are defined as for the compounds of group 1, or pharmaceutically acceptable tautomers, enantiomers, diastereomers, salts or solvates thereof.

For the compounds of group 1, 1.a, 1.b, 1.c and 1.d according to formula (I)

R² is preferably (a) a $C_{1-4}$-alkyl- or $C_{2-5}$-alkenyl-group,
optionally substituted by one or more substituents independently selected from the group consisting of pyridinyl-, thienyl-, phenyl- or cyclohexyl-groups,
wherein the phenyl group may be optionally substituted by one or more substituents independently selected from the group consisting of hydroxymethyl-, cyano-, halogen, hydroxy-, carboxy-, nitro-, $H_2N$—CO—, $H_2N$— or Me-NH—CO—NH-groups, or (b) a bicyclic carbocyclic ring,
optionally substituted by one or more substituents independently selected from the group consisting of $C_{1-3}$-alkyl-, halogen, hydroxy-, carboxy-, nitro-, $H_2N$—CO— or $H_2N$-groups, more preferably R² is an ethyl-group,
or a substituent selected from the group consisting of

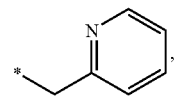

2.1

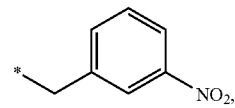

2.2

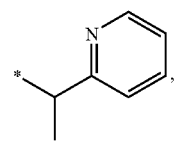

2.3

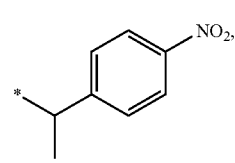

2.4

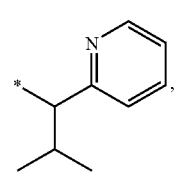

2.5

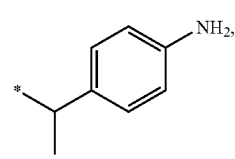

2.6

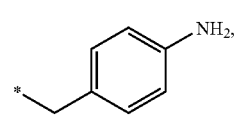

2.7

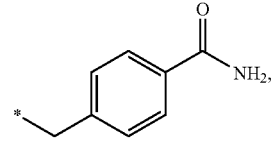

2.8

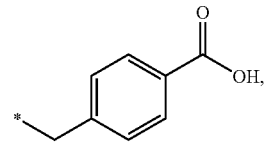

2.9

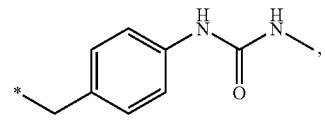

2.10

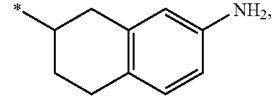

2.11

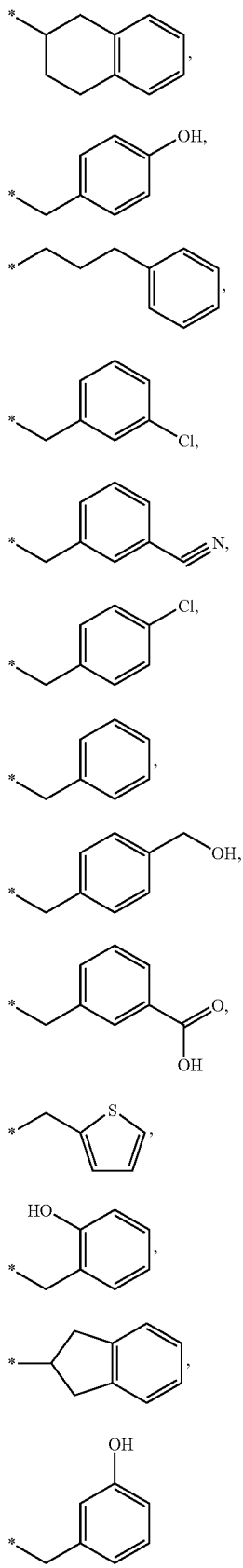

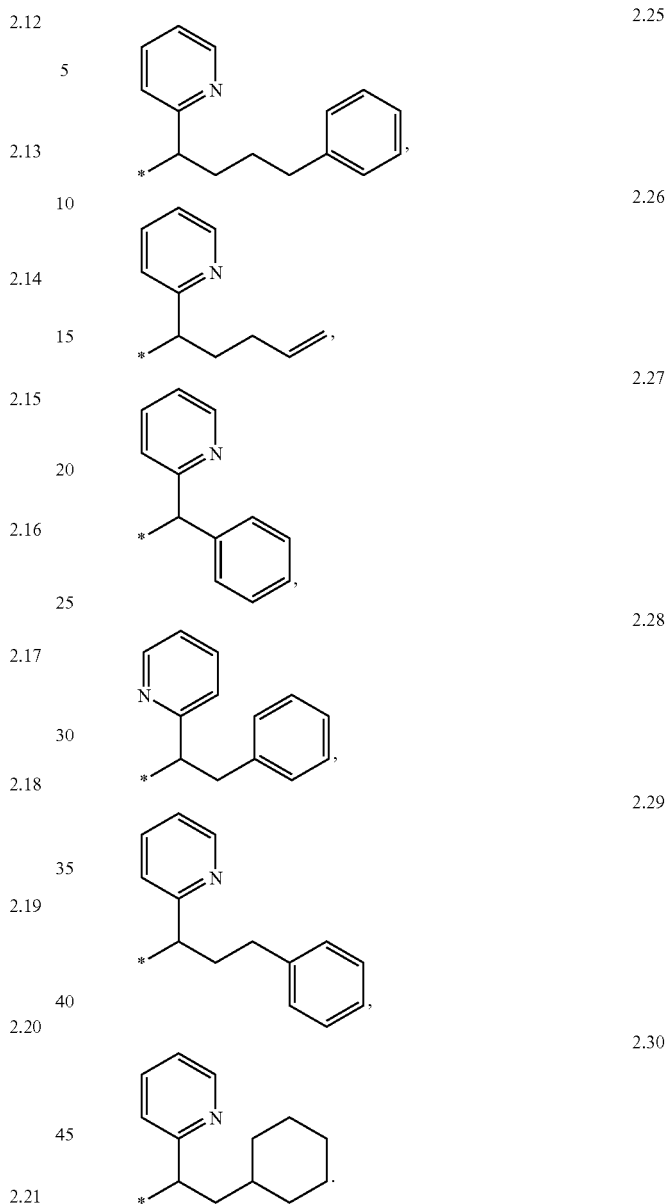

For the compounds of group 1, 1.a, 1.b, 1.c and 1.d according to formula (I)

$R^3$ is preferably a n-propyl-, 2-methylpropyl-, 2,2-dimethylpropyl-, 1-methylpropyl-, 3-methylbutyl-, ethyl-, or a cyclopropylmethyl-group, more preferably $R^3$ is a 1-methylpropyl- or a 2,2-dimethylpropyl-group.

For the compounds of group 1, 1.a, 1.b, 1.c and 1.d according to formula (I)

$R^4$ is preferably a methyl-, n-propyl-, 1-methylpropyl-, methoxymethyl-, prop-2-enyl-, cyclopropylmethyl-, aminocarbonylmethyl-, phenyl-, 2-phenylethyl-, 3-phenylpropyl-, 2-(4-hydroxyphenyl)ethyl-, 2-(4-methoxyphenyl)ethyl-, benzyloxymethyl or a indol-3-ylmethyl-group, more preferably R$^4$ is a n-propyl-, prop-2-enyl- or a cyclopropylmethyl-group.

For the compounds of group 1, 1.a, 1.b, 1.c and 1.d according to formula (I)

R$^5$ is preferably a n-propyl-, 2-methylpropyl-, n-butyl-, methylthioethyl-, cyclohexylmethyl-, benzyl- or a 3,5-difluorbenzyl-group, more preferably R$^5$ is a 2-methylpropyl- or a 3,5-difluorbenzyl-group.

For the compounds of group 1, 1.a, 1.b, 1.c and 1.d according to formula (I)

R$^6$ and R$^7$ each independently preferably represent hydrogen or fluor, more preferably R$^6$ and R$^7$ represent hydrogen.

For the compounds of group 1, 1.a, 1.b, 1.c and 1.d according to formula (I)

R$^8$ preferably is hydrogen.

Accordingly, preferred are the compounds according to the groups 1, 1.a, 1.b, 1.c or 1.d wherein R$^2$ represents
  (a) a $C_{1-4}$-alkyl- or $C_{1-5}$-alkenyl-group,
    optionally substituted by one or more substituents independently selected from the group consisting of pyridinyl-, thienyl-, phenyl- or cyclohexyl-groups,
      wherein the phenyl group may be optionally substituted by one or more substituents independently selected from the group consisting of hydroxymethyl-, cyano-, halogen, hydroxy-, carboxy-, nitro-, H$_2$N—CO—, H$_2$N— or Me-NH—CO—NH-groups, or
  (b) a bicyclic carbocyclic ring,
    optionally substituted by one or more substituents independently selected from the group consisting of $C_{1-3}$-alkyl-, halogen, hydroxy-, carboxy-, nitro-, H$_2$N—CO— or H$_2$N-groups.

Furtheron preferred are the compounds according to the groups 1, 1.a, 1.b, 1.c or 1.d wherein R$^3$ represents a n-propyl-, 2-methylpropyl-, 2,2-dimethylpropyl-, 1-methylpropyl-, 3-methylbutyl-, ethyl-, or a cyclopropylmethyl-group.

Furtheron preferred are the compounds according to the groups 1, 1.a, 1.b, 1.c or 1.d wherein R$^4$ represents a methyl-, n-propyl-, 1-methylpropyl-, methoxymethyl-, prop-2-enyl-, cyclopropylmethyl-, aminocarbonylmethyl-, phenyl-, 2-phenylethyl-, 3-phenylpropyl-, 2-(4-hydroxyphenyl)ethyl-, 2-(4-methoxyphenyl)ethyl-, benzyloxymethyl or a indol-3-ylmethyl-group.

Furtheron preferred are the compounds according to the groups 1, 1.a, 1.b, 1.c or 1.d wherein R$^5$ represents a n-propyl-, 2-methylpropyl-, n-butyl-, methylthioethyl-, cyclohexylmethyl-, benzyl- or a 3,5-difluorbenzyl-group.

Furtheron preferred are the compounds according to the groups 1, 1.a, 1.b, 1.c or 1.d wherein R$^2$ represents
  (a) a $C_{1-4}$-alkyl- or $C_{1-5}$-alkenyl-group,
    optionally substituted by one or more substituents independently selected from the group consisting of pyridinyl-, thienyl-, phenyl- or cyclohexyl-groups,
      wherein the phenyl group may be optionally substituted by one or more substituents independently selected from the group consisting of hydroxymethyl-, cyano-, halogen, hydroxy-, carboxy-, nitro-, H$_2$N—CO—, H$_2$N— or Me-NH—CO—NH-groups, or
  (b) a bicyclic carbocyclic ring,
    optionally substituted by one or more substituents independently selected from the group consisting of $C_{1-3}$-alkyl-, halogen, hydroxy-, carboxy-, nitro-, H$_2$N—CO— or H$_2$N-groups, and R$^3$ represents a n-propyl-, 2-methylpropyl-, 2,2-dimethylpropyl-, 1-methylpropyl-, 3-methylbutyl-, ethyl-, or a cyclopropylmethyl-group.

Furtheron preferred are the compounds according to the groups 1, 1.a, 1.b, 1.c or 1.d wherein R$^2$ represents
  (a) a $C_{1-4}$-alkyl- or $C_{1-5}$-alkenyl-group,
    optionally substituted by one or more substituents independently selected from the group consisting of pyridinyl-, thienyl-, phenyl- or cyclohexyl-groups,
      wherein the phenyl group may be optionally substituted by one or more substituents independently selected from the group consisting of hydroxymethyl-, cyano-, halogen, hydroxy-, carboxy-, nitro-, H$_2$N—CO—, H$_2$N— or Me-NH—CO—NH-groups, or
  (b) a bicyclic carbocyclic ring,
    optionally substituted by one or more substituents independently selected from the group consisting of $C_{1-3}$-alkyl-, halogen, hydroxy-, carboxy-, nitro-, H$_2$N—CO— or H$_2$N-groups, and R$^4$ represents a methyl-, n-propyl-, 1-methylpropyl-, methoxymethyl-, prop-2-enyl-, cyclopropylmethyl-, aminocarbonylmethyl-, phenyl-, 2-phenylethyl-, 3-phenylpropyl-, 2-(4-hydroxyphenyl)ethyl-, 2-(4-methoxyphenyl)ethyl-, benzyloxymethyl or a indol-3-ylmethyl-group.

Furtheron preferred are the compounds according to the groups 1, 1.a, 1.b, 1.c or 1.d wherein R$^1$ represents
  (a) a $C_{1-4}$-alkyl- or $C_{1-5}$-alkenyl-group,
    optionally substituted by one or more substituents independently selected from the group consisting of pyridinyl-, thienyl-, phenyl- or cyclohexyl-groups,
      wherein the phenyl group may be optionally substituted by one or more substituents independently selected from the group consisting of hydroxymethyl-, cyano-, halogen, hydroxy-, carboxy-, nitro-, H$_2$N—CO—, H$_2$N— or Me-NH—CO—NH-groups, or
  (b) a bicyclic carbocyclic ring, optionally substituted by one or more substituents independently selected from the group consisting of $C_{1-3}$-alkyl-, halogen, hydroxy-, carboxy-, nitro-, H$_2$N—CO— or H$_2$N-groups, and R$^5$ represents a n-propyl-, 2-methylpropyl-, n-butyl-, methylthioethyl-, cyclohexylmethyl-, benzyl- or a 3,5-difluorbenzyl-group.

Furtheron preferred are the compounds according to the groups 1, 1.a, 1.b, 1.c or 1.d wherein $R^3$ represents a n-propyl-, 2-methylpropyl-, 2,2-dimethylpropyl-, 1-methylpropyl-, 3-methylbutyl-, ethyl-, or a cyclopropylmethyl-group, and $R^4$ represents a methyl-, n-propyl-, 1-methylpropyl-, methoxymethyl-, prop-2-enyl-, cyclopropylmethyl-, aminocarbonylmethyl-, phenyl-, 2-phenylethyl-, 3-phenylpropyl-, 2-(4-hydroxyphenyl)ethyl-, 2-(4-methoxyphenyl)ethyl-, benzyloxymethyl or a indol-3-ylmethyl-group.

Furtheron preferred are the compounds according to the groups 1, 1.a, 1.b, 1.c or 1.d wherein $R^3$ represents a n-propyl-, 2-methylpropyl-, 2,2-dimethylpropyl-, 1-methylpropyl-, 3-methylbutyl-, ethyl-, or a cyclopropylmethyl-group, and $R^5$ represents a n-propyl-, 2-methylpropyl-, n-butyl-, methylthioethyl-, cyclohexylmethyl-, benzyl- or a 3,5-difluorbenzyl-group.

Furtheron preferred are the compounds according to the groups 1, 1.a, 1.b, 1.c or 1.d wherein $R^4$ represents a methyl-, n-propyl-, 1-methylpropyl-, methoxymethyl-, prop-2-enyl-, cyclopropylmethyl-, aminocarbonylmethyl-, phenyl-, 2-phenylethyl-, 3-phenylpropyl-, 2-(4-hydroxyphenyl)ethyl-, 2-(4-methoxyphenyl)ethyl-, benzyloxymethyl or a indol-3-ylmethyl-group, and $R^5$ represents a n-propyl-, 2-methylpropyl-, n-butyl-, methylthioethyl-, cyclohexylmethyl-, benzyl- or a 3,5-difluorbenzyl-group.

Furtheron preferred are the compounds according to the groups 1, 1.a, 1.b, 1.c or 1.d wherein $R^2$ represents (a) a $C_{1-4}$-alkyl- or $C_{1-5}$-alkenyl-group, optionally substituted by one or more substituents independently selected from the group consisting of pyridinyl-, thienyl-, phenyl- or cyclohexyl-groups, wherein the phenyl group may be optionally substituted by one or more substituents independently selected from the group consisting of hydroxymethyl-, cyano-, halogen, hydroxy-, carboxy-, nitro-, $H_2N$—CO—, $H_2N$— or Me-NH—CO—NH-groups, or (b) a bicyclic carbocyclic ring, optionally substituted by one or more substituents independently selected from the group consisting of $C_{1-3}$-alkyl-, halogen, hydroxy-, carboxy-, nitro-, $H_2N$—CO— or $H_2N$-groups, and $R^3$ represents a n-propyl-, 2-methylpropyl-, 2,2-dimethylpropyl-, 1-methylpropyl-, 3-methylbutyl-, ethyl-, or a cyclopropylmethyl-group, and $R^4$ represents a methyl-, n-propyl-, 1-methylpropyl-, methoxymethyl-, prop-2-enyl-, cyclopropylmethyl-, aminocarbonylmethyl-, phenyl-, 2-phenylethyl-, 3-phenylpropyl-, 2-(4-hydroxyphenyl)ethyl-, 2-(4-methoxyphenyl)ethyl-, benzyloxymethyl or a indol-3-ylmethyl-group.

Furtheron preferred are the compounds according to the groups 1, 1.a, 1.b, 1.c or 1.d wherein $R^2$ represents (a) a $C_{1-4}$-alkyl- or $C_{1-5}$-alkenyl-group, optionally substituted by one or more substituents independently selected from the group consisting of pyridinyl-, thienyl-, phenyl- or cyclohexyl-groups, wherein the phenyl group may be optionally substituted by one or more substituents independently selected from the group consisting of hydroxymethyl-, cyano-, halogen, hydroxy-, carboxy-, nitro-, $H_2N$—CO—, $H_2N$— or Me-NH—CO—NH-groups, or (b) a bicyclic carbocyclic ring, optionally substituted by one or more substituents independently selected from the group consisting of $C_{1-3}$-alkyl-, halogen, hydroxy-, carboxy-, nitro-, $H_2N$—CO— or $H_2N$-groups, and $R^3$ represents a n-propyl-, 2-methylpropyl-, 2,2-dimethylpropyl-, 1-methylpropyl-, 3-methylbutyl-, ethyl-, or a cyclopropylmethyl-group, and $R^5$ represents a n-propyl-, 2-methylpropyl-, n-butyl-, methylthioethyl-, cyclohexylmethyl-, benzyl- or a 3,5-difluorbenzyl-group.

Furtheron preferred are the compounds according to the groups 1, 1.a, 1.b, 1.c or 1.d wherein $R^2$ represents (a) a $C_{1-4}$-alkyl- or $C_{1-5}$-alkenyl-group, optionally substituted by one or more substituents independently selected from the group consisting of pyridinyl-, thienyl-, phenyl- or cyclohexyl-groups, wherein the phenyl group may be optionally substituted by one or more substituents independently selected from the group consisting of hydroxymethyl-, cyano-, halogen, hydroxy-, carboxy-, nitro-, $H_2N$—CO—, $H_2N$— or Me-NH—CO—NH-groups, or (b) a bicyclic carbocyclic ring, optionally substituted by one or more substituents independently selected from the group consisting of $C_{1-3}$-alkyl-, halogen, hydroxy-, carboxy-, nitro-, $H_2N$—CO— or $H_2N$-groups, and $R^4$ represents a methyl-, n-propyl-, 1-methylpropyl-, methoxymethyl-, prop-2-enyl-, cyclopropylmethyl-, aminocarbonylmethyl-, phenyl-, 2-phenylethyl-, 3-phenylpropyl-, 2-(4-hydroxyphenyl)ethyl-, 2-(4-methoxyphenyl)ethyl-, benzyloxymethyl or a indol-3-ylmethyl-group, and $R^5$ represents a n-propyl-, 2-methylpropyl-, n-butyl-, methylthioethyl-, cyclohexylmethyl-, benzyl- or a 3,5-difluorbenzyl-group.

Furtheron preferred are the compounds according to the groups 1, 1.a, 1.b, 1.c or 1.d wherein $R^3$ represents a n-propyl-, 2-methylpropyl-, 2,2-dimethylpropyl-, 1-methylpropyl-, 3-methylbutyl-, ethyl-, or a cyclopropylmethyl-group, and $R^4$ represents a methyl-, n-propyl-, 1-methylpropyl-, methoxymethyl-, prop-2-enyl-, cyclopropylmethyl-, aminocarbonylmethyl-, phenyl-, 2-phenylethyl-, 3-phenylpropyl-, 2-(4-hydroxyphenyl)ethyl-, 2-(4-methoxyphenyl)ethyl-, benzyloxymethyl or a indol-3-ylmethyl-group, and $R^5$ represents a n-propyl-, 2-methylpropyl-, n-butyl-, methylthioethyl-, cyclohexylmethyl-, benzyl- or a 3,5-difluorbenzyl-group.

A more preferred embodiment the present invention relates to compounds of group 1.e according to formula (I), wherein $R^1$ represents
 a) a carboxy-$C_{1-6}$-alkyl-,
 b) a $C_{1-6}$-alkyl-O—CO—$C_{1-6}$-alkyl-,
 c) a $C_{3-8}$-cycloalkyl- or $C_{3-8}$-cycloalkyl-$C_{1-3}$-alkyl-,
 d) a heterocyclyl-,
 e) a aryl-, or a aryl-$C_{1-3}$-alkyl-, or
 f) a heteroaryl-group
  wherein each of said groups may be optionally substituted by one or more substituents independently selected from the group consisting of $C_{1-6}$-alkyl-, aryl-CO—, C 16-alkyl-O—, $C_{1-6}$-alkyl-O—CO—, $C_{1-6}$-alkyl-CO—, $C_{1-6}$-alkyl-CO—$NR^8$—, halogen-, carboxy-, hydroxy-, nitro-, oxo- or $(R^8)_2N$—$SO_2$-groups, $R^2$ represents
 (a) a $C_{1-4}$-alkyl- or $C_{1-5}$-alkenyl-group,
  optionally substituted by one or more substituents independently selected from the group consisting of pyridinyl-, thienyl-, phenyl- or cyclohexyl-groups,
   wherein the phenyl group may be optionally substituted by one or more substituents independently selected from the group consisting of hydroxymethyl-, cyano-, halogen, hydroxy-, carboxy-, nitro-, $H_2N$—CO—, $H_2N$— or Me-NH—CO—NH-groups, or
 (b) a bicyclic carbocyclic ring,
  optionally substituted by one or more substituents independently selected from the group consisting of $C_{1-3}$-alkyl-, halogen, hydroxy-, carboxy-, nitro-, $H_2N$—CO— or $H_2N$-groups, $R^3$ represents a n-propyl-, 2-methylpropyl-, 2,2-dimethylpropyl-, 1-methylpropyl-, 3-methylbutyl-, ethyl-, or a cyclopropylmethyl-group, $R^4$ represents a methyl-, n-propyl-, 1-methylpropyl-, methoxymethyl-, prop-2-enyl-, cyclopropylmethyl-, aminocarbonylmethyl-, phenyl-, 2-phenylethyl-, 3-phenylpropyl-, 2-(4-hydroxyphenyl)ethyl-, 2-(4-methoxyphenyl)ethyl-, benzyloxymethyl or a indol-3-ylmethyl-group, $R^5$ represents a n-propyl-, 2-methylpropyl-, n-butyl-, methylthioethyl-, cyclohexylmethyl-, benzyl- or a 3,5-difluorbenzyl-group, $R^6$ and $R^7$ each independently represent hydrogen or a halogen atom, preferably hydrogen or a fluor atom, more preferably hydrogen, $R^8$ represents hydrogen or a $C_{1-6}$-alkyl-group, preferably a hydrogen, or pharmaceutically acceptable tautomers, enantiomers, diastereomers, salts or solvates thereof.

In a further preferred embodiment the present invention relates to compounds of group 1.f according to formula (I), wherein $R^1$ represents a group selected from a 3-carboxypropyl-, 3-methoxycarbonylpropyl-, 1-methyl-cyclohexyl, 1-acetylpiperidin-3-yl-, 1-benzoylpiperidin-3-yl-, phenyl-, 3-carboxyphenyl-, 3-hydroxyphenyl-, 4-hydroxyphenyl-, 2-fluoro-4-hydroxyphenyl-, 3-fluoro-4-hydroxyphenyl-, 3-chloro-4-hydroxyphenyl-, 3,5-dichloro-4-hydroxyphenyl-, 3-acetylaminophenyl-, 3-acetylphenyl-, 4-methoxyphenyl-, 3-nitrophenyl-, 4-nitrophenyl-, 3-nitro-4-hydroxyphenyl-, 4-methoxycarbonylphenyl-, 3-methoxycarbonylphenyl-, 4-hydroxy-2,3,5,6-tetrafluorophenyl-, 4-sulfamoylphenyl-, 3-hydroxybenzyl-, 4-hydroxybenzyl-, 1-(4-hydroxyphenyl)-2-methylpropyl-, 5-hydroxypyrazin-2-yl-, 6-hydroxypyridin-3-yl-, 6-oxo-1,6-dihydropyridazin-3-yl-, pyridin-2-yl, pyridin-3-yl-, pyridin-4-yl-, pyridin-2-yl N-oxide, pyridin-3-yl N-oxide or a pyridin-4-yl N-oxide group, and $R^2$, $R^3$, $R^4$, $R^5$, $R^6$ and $R^7$ are defined as for the compounds of group 1.e, or pharmaceutically acceptable tautomers, enantiomers, diastereomers, salts or solvates thereof.

In a further preferred embodiment the present invention relates to compounds of group 1.g according to formula (I), wherein $R^1$ represents a group selected from a carboxy-$C_{1-6}$-alkyl-, pyridin-2-yl N-oxide, pyridin-3-yl N-oxide, pyridin-4-yl N-oxide or a phenyl-group,
 wherein the phenyl group is substituted by one or more substituents independently selected from the group consisting of hydroxy groups, carboxy groups or halogen atoms, preferably fluor atoms and hydroxy groups, and $R^2$, $R^3$, $R^4$, $R^5$, $R^6$ and $R^7$ are defined as for the compounds of group 1.e, or pharmaceutically acceptable tautomers, enantiomers, diastereomers, salts or solvates thereof.

In a further preferred embodiment the present invention relates to compounds of group 1.h according to formula (I), wherein $R^1$ represents a group selected from a 3-carboxypropyl-, pyridin-4-yl N-oxide, 3-carboxyphenyl- or a 4-hydroxy-2,3,5,6-tetrafluorophenyl-group, and $R^2$, $R^3$, $R^4$, $R^5$, $R^6$ and $R^7$ are defined as for the compounds of group 1.e, or pharmaceutically acceptable tautomers, enantiomers, diastereomers, salts or solvates thereof.

In a further preferred embodiment the present invention relates to compounds of group 1.i according to formula (I), wherein $R^1$ represents a group selected from a 3-carboxypropyl- or a pyridin-4-yl N-oxide-group, and $R^2$, $R^3$, $R^4$, $R^5$, $R^6$, $R^7$ and $R^8$ are defined as for the compounds of group 1.e, or pharmaceutically acceptable tautomers, enantiomers, diastereomers, salts or solvates thereof.

Furtheron preferred are the compounds according to the groups 1, 1.a, 1.b, 1.c, 1.d, 1.e, 1.f, 1.g, 1.h or 1.i wherein R² represents an ethyl-group,
or a substituent selected from the group consisting of
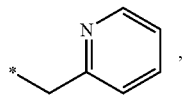  2.1
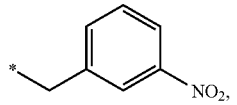  2.2
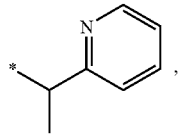  2.3
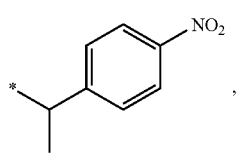  2.4
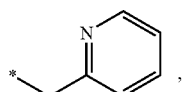  2.5
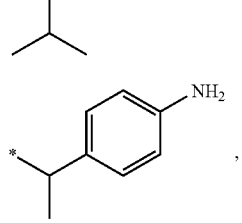  2.6
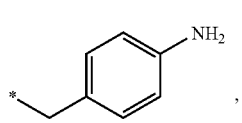  2.7
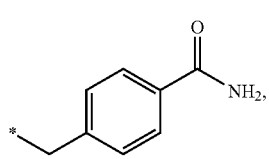  2.8
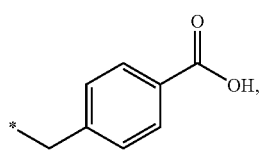  2.9
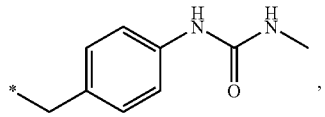  2.10
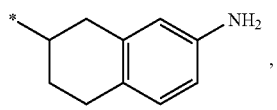  2.11
-continued
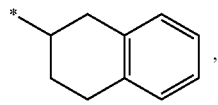  2.12
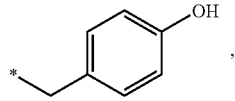  2.13
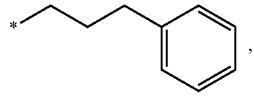  2.14
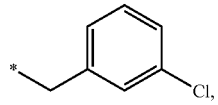  2.15
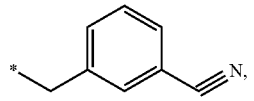  2.16
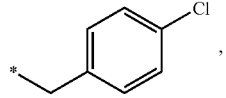  2.17
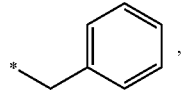  2.18
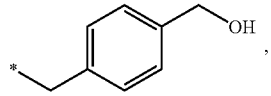  2.19
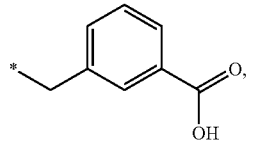  2.20
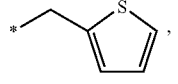  2.21
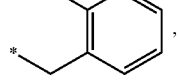  2.22
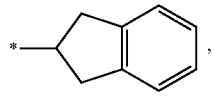  2.23
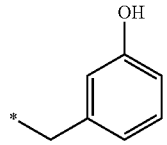  2.24

-continued 2.25 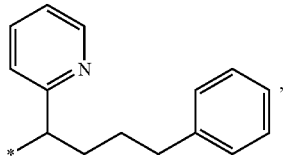, 2.26 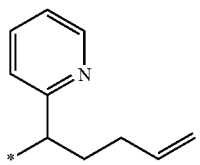, 2.27 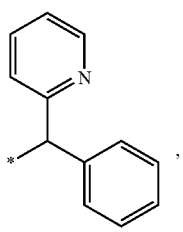, 2.28 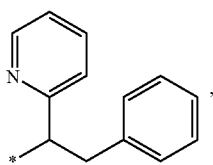, 2.29 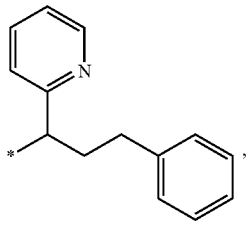, 2.30 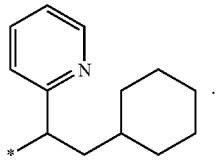.

Furtheron preferred are the compounds according to the groups 1, 1.a, 1.b, 1.c, 1.d, 1.e, 1.f, 1.g, 1.h or 1.i wherein
R³ represents a 1-methylpropyl- or a 2,2-dimethylpropyl-group.

Furtheron preferred are the compounds according to the groups 1, 1.a, 1.b, 1.c, 1.d, 1.e, 1.f, 1.g, 1.h or 1.i wherein
R⁴ represents a n-propyl-, prop-2-enyl- or a cyclopropylmethyl-group.

Furtheron preferred are the compounds according to the groups 1, 1.a, 1.b, 1.c, 1.d, 1.e, 1.f, 1.g, 1.h or 1.i wherein
R⁵ represents a 2-methylpropyl- or a 3,5-difluorbenzyl-group.

Furtheron preferred are the compounds according to the groups 1, 1.a, 1.b, 1.c, 1.d, 1.e, 1.f, 1.g, 1.h or 1.i wherein
R² represents an ethyl-group, or a substituent selected from the group consisting of 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29 or 2.30 as defined above, and R³ represents a 1-methylpropyl- or a 2,2-dimethylpropyl-group.

Furtheron preferred are the compounds according to the groups 1, 1.a, 1.b, 1.c, 1.d, 1.e, 1.f, 1.g, 1.h or 1.i wherein
R² represents an ethyl-group, or a substituent selected from the group consisting of 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29 or 2.30 as defined above, and R⁴ represents a n-propyl-, prop-2-enyl- or a cyclopropylmethyl-group.

Furtheron preferred are the compounds according to the groups 1, 1.a, 1.b, 1.c, 1.d, 1.e, 1.f, 1.g, 1.h or 1.i wherein
R² represents an ethyl-group, or a substituent selected from the group consisting of 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29 or 2.30 as defined above, and R⁵ represents a 2-methylpropyl- or a 3,5-difluorbenzyl-group.

Furtheron preferred are the compounds according to the groups 1, 1.a, 1.b, 1.c, 1.d, 1.e, 1.f, 1.g, 1.h or 1.i wherein
R³ represents a 1-methylpropyl- or a 2,2-dimethylpropyl-group, and R⁴ represents a n-propyl-, prop-2-enyl- or a cyclopropylmethyl-group.

Furtheron preferred are the compounds according to the groups 1, 1.a, 1.b, 1.c, 1.d, 1.e, 1.f, 1.g, 1.h or 1.i wherein
R³ represents a 1-methylpropyl- or a 2,2-dimethylpropyl-group, and R⁵ represents a 2-methylpropyl- or a 3,5-difluorbenzyl-group.

Furtheron preferred are the compounds according to the groups 1, 1.a, 1.b, 1.c, 1.d, 1.e, 1.f, 1.g, 1.h or 1.i wherein
R⁴ represents a n-propyl-, prop-2-enyl- or a cyclopropylmethyl-group, and R⁵ represents a 2-methylpropyl- or a 3,5-difluorbenzyl-group.

Furtheron preferred are the compounds according to the groups 1, 1.a, 1.b, 1.c, 1.d, 1.e, 1.f, 1.g, 1.h or 1.i wherein
R² represents an ethyl-group, or a substituent selected from the group consisting of 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29 or 2.30 as defined above, and R³ represents a 1-methylpropyl- or a 2,2-dimethylpropyl-group, and R⁴ represents a n-propyl-, prop-2-enyl- or a cyclopropylmethyl-group.

Furtheron preferred are the compounds according to the groups 1, 1.a, 1.b, 1.c, 1.d, 1.e, 1.f, 1.g, 1.h or 1.i wherein
$R^2$ represents an ethyl-group, or a substituent selected from the group consisting of 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29 or 2.30 as defined above, and $R^3$ represents a 1-methylpropyl- or a 2,2-dimethylpropyl-group, and $R^5$ represents a 2-methylpropyl- or a 3,5-difluorbenzyl-group.

Furtheron preferred are the compounds according to the groups 1, 1.a, 1.b, 1.c, 1.d, 1.e, 1.f, 1.g, 1.h or 1.i wherein
$R^2$ represents an ethyl-group, or a substituent selected from the group consisting of 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29 or 2.30 as defined above, and $R^4$ represents a n-propyl-, prop-2-enyl- or a cyclopropylmethyl-group, and $R^5$ represents a 2-methylpropyl- or a 3,5-difluorbenzyl-group.

Furtheron preferred are the compounds according to the groups 1, 1.a, 1.b, 1.c, 1.d, 1.e, 1.f, 1.g, 1.h or 1.i wherein
$R^3$ represents a 1-methylpropyl- or a 2,2-dimethylpropyl-group, and $R^4$ represents a n-propyl-, prop-2-enyl- or a cyclopropylmethyl-group, and $R^5$ represents a 2-methylpropyl- or a 3,5-diflorbenzyl-group.

Furtheron preferred are the compounds according to the groups 1, 1.a, 1.b, 1.c, 1.d, 1.e, 1.f, 1.g, 1.h or 1.i wherein
$R^2$ represents an ethyl-group, or a substituent selected from the group consisting of 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29 or 2.30 as defined above, and $R^3$ represents a 1-methylpropyl- or a 2,2-dimethylpropyl-group, and $R^4$ represents a n-propyl-, prop-2-enyl- or a cyclopropylmethyl-group, and $R^5$ represents a 2-methylpropyl- or a 3,5-difluorbenzyl-group.

Most preferred are the compounds of Example (1) through (38):

| Structure | Example # |
| --- | --- |
| 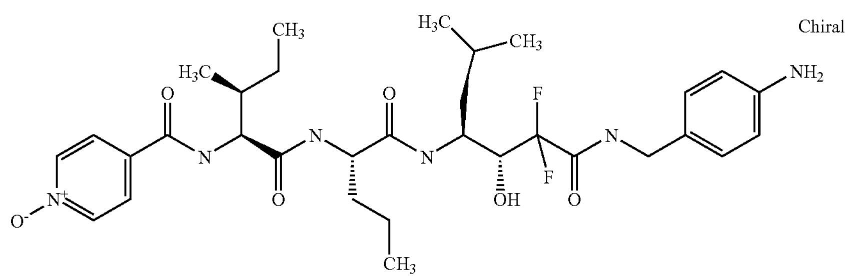 | (1) |
| 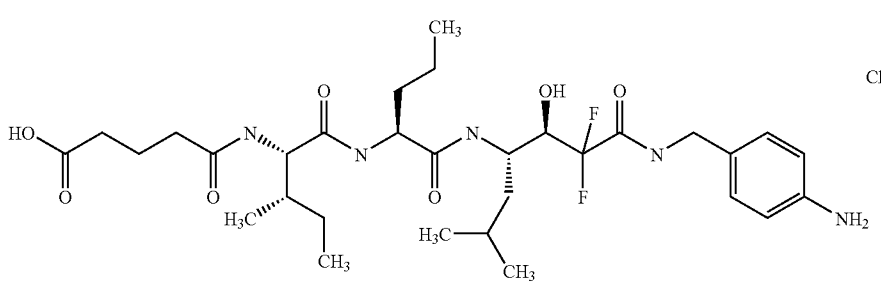 | (2) |

| Structure | Example # |
|---|---|
| 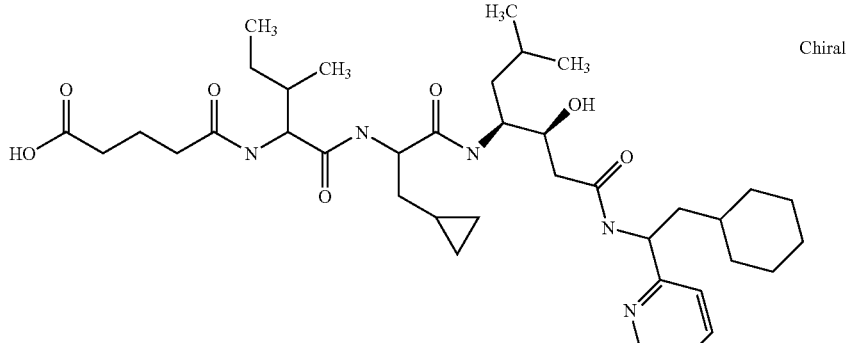 | (3) Chiral |
| 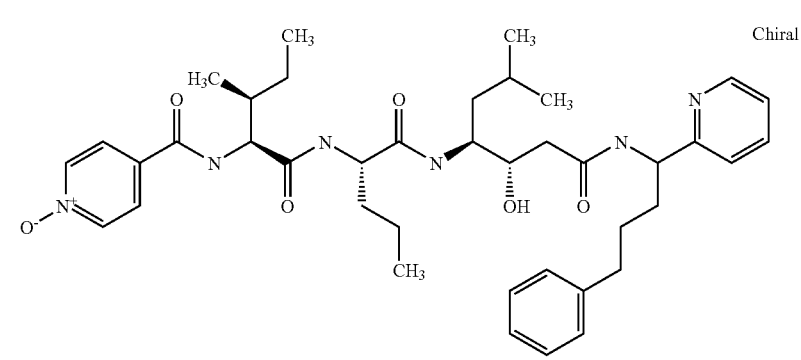 | (4) Chiral |
| 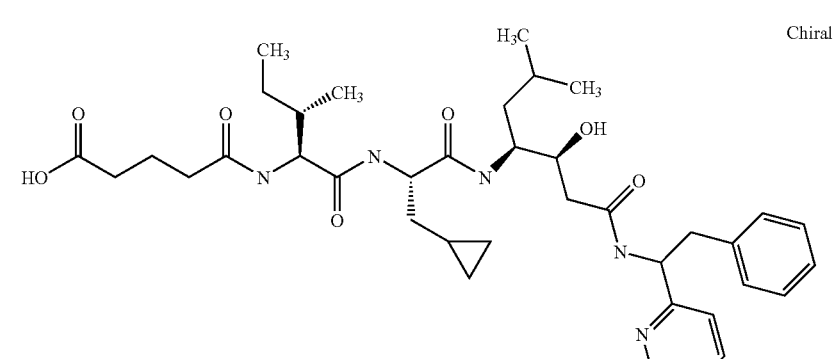 | (5) Chiral |
| 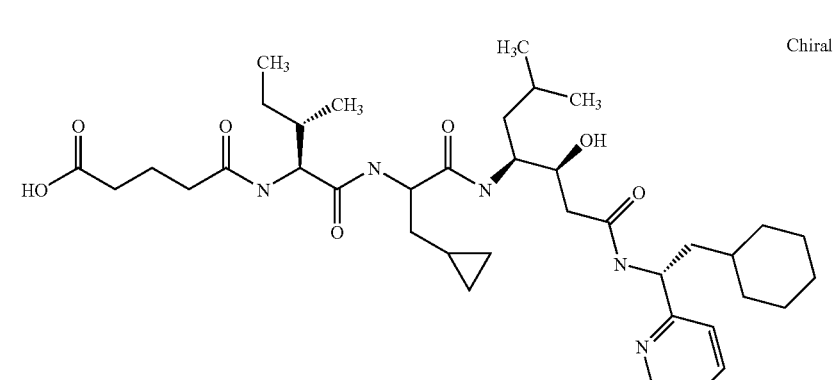 | (6) Chiral |

-continued
| Structure | Example # |
|---|---|
| 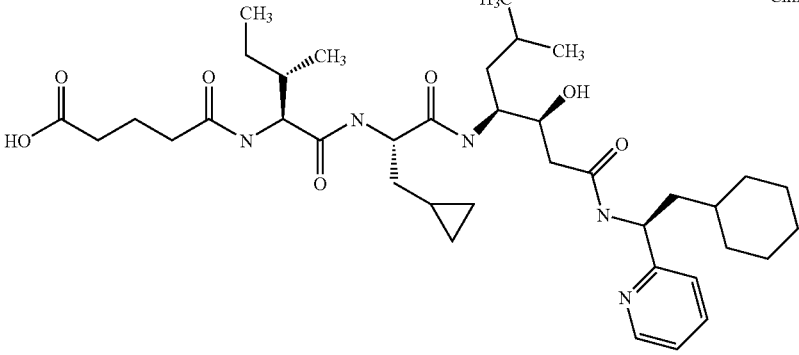 | Chiral (7) |
| 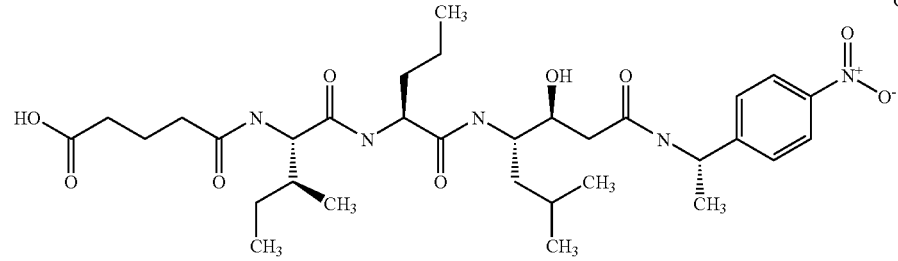 | Chiral (8) |
| 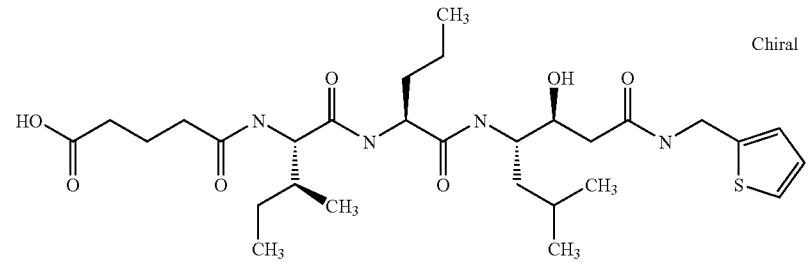 | (9) Chiral |
| 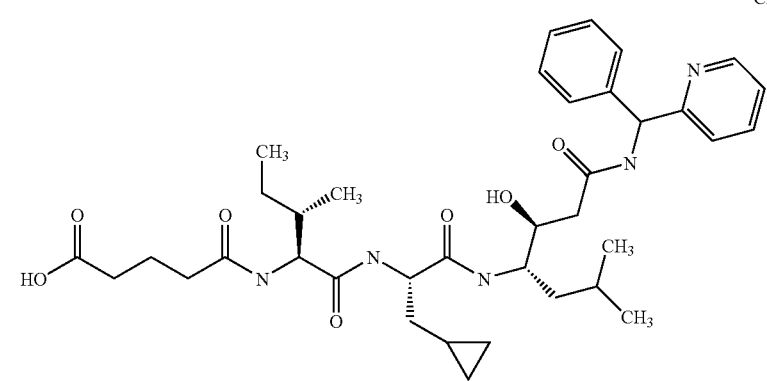 | Chiral (10) |

| Structure | Example # |
|---|---|
| (chemical structure) | (11) |
| (chemical structure) | (12) |
| (chemical structure) | (13) |
| (chemical structure) | (14) |
| (chemical structure) | (15) |

-continued

| Structure | Example # |
|---|---|
| (chemical structure) | (16) Chiral |
| (chemical structure) | (17) Chiral |
| (chemical structure) | (18) Chiral |
| (chemical structure) | (19) Chiral |

-continued
| Structure | Example # |
|---|---|
| 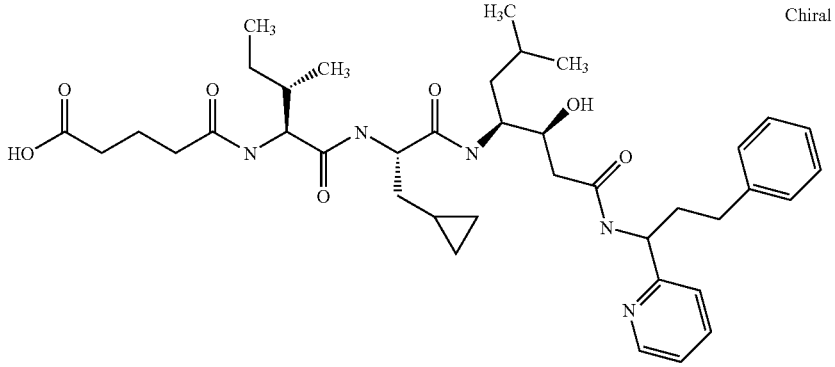 Chiral | (20) |
| 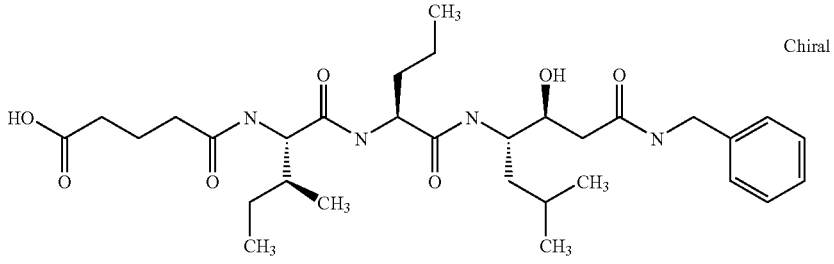 Chiral | (21) |
| 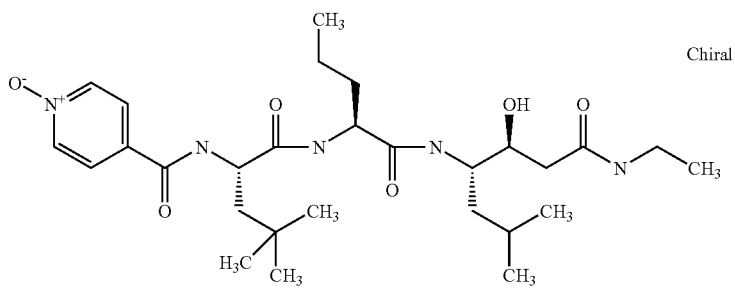 Chiral | (22) |
| 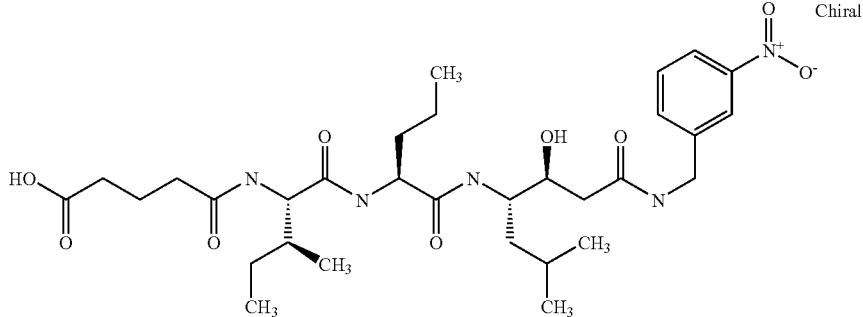 Chiral | (23) |

| Structure | Example # |
|---|---|
| (chemical structure) | (24) |
| (chemical structure) | (25) |
| (chemical structure) | (26) |
| (chemical structure) | (27) |
| (chemical structure) | (28) |

| Structure | Example # |
|---|---|
| (chemical structure) | (29) |
| (chemical structure) | (30) |
| (chemical structure) | (31) |
| (chemical structure) | (32) |
| (chemical structure) | (33) |

| Structure | Example # |
|---|---|
| 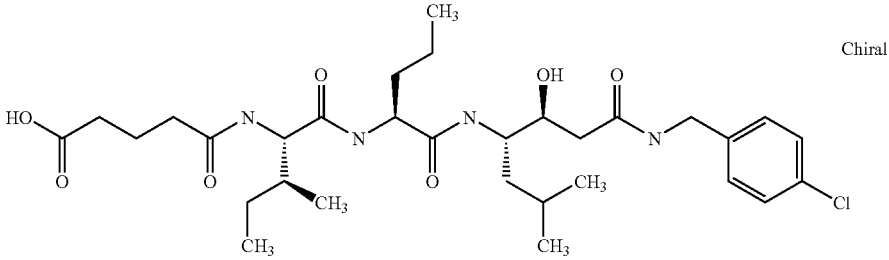 | (34) |
| 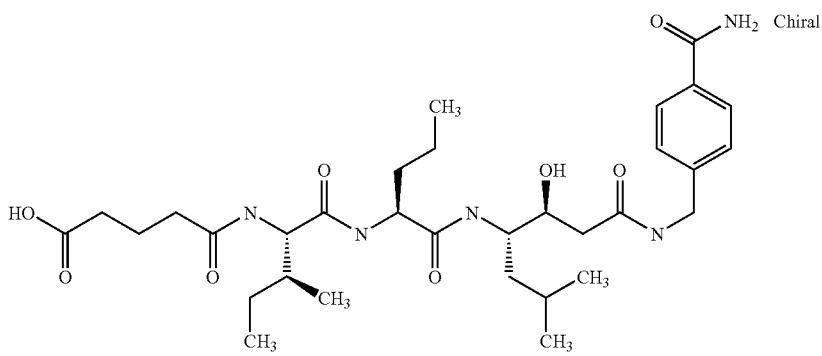 | (35) |
| 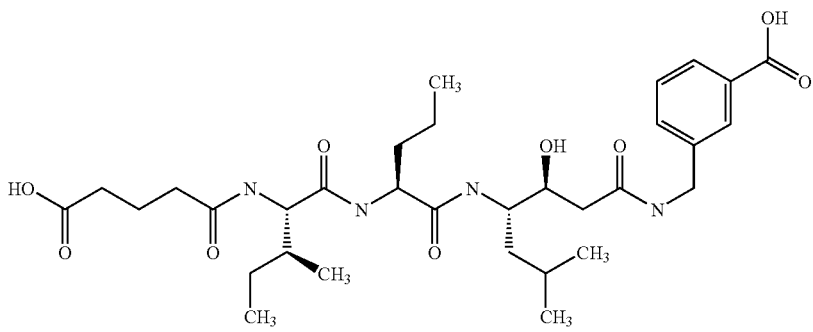 | (36) |
| 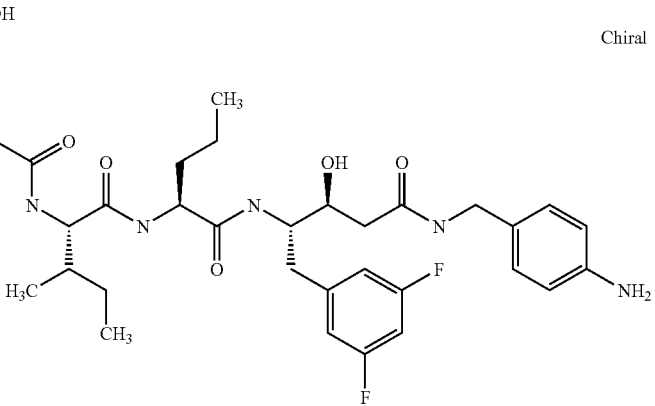 | (37) |

-continued

| Structure | Example # |
|---|---|
| 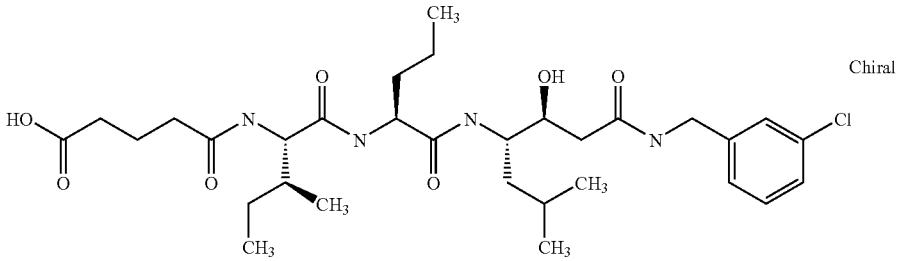 | (38) |

The anti-Alzheimer's compounds of the present invention are made by methods well known to those skilled in the art from starting compounds known to those skilled in the art. The process chemistry is well known to those skilled in the art. The following reaction schemes illustrate the peptide synthesis of the compounds according to the present invention.

One skilled in the art will appreciate that these are all well known reactions in organic chemistry (Houben-Weyl—Methods of Organic Chemistry, Vol E22, Synthesis of Peptides and Peptidomimetics, M. Goodman, A. Felix, L. Moroder, C. Toniolo Eds., Georg Thieme Verlag Stuttgart, New York). A chemist skilled in the art, knowing the chemical structure of the biologically active compounds according to formula (I) of the invention would be able to prepare them by known methods from known starting materials without any additional information. The explanation below therefore is not necessary but is deemed helpful to those skilled in the art who desire to make the compounds of the present invention.

As illustrated in schema A peptides bearing a N-ethyl amide at the C-terminus were synthesized by solid phase synthesis using a commercially available [3-{[ethyl-Fmoc-amino]-methyl}-indol-1-yl-acetyl AM resin (Indol resin, Novabiochem). After cleavage of the Fmoc-group with piperidine in DMF (step a) the first amino acid is coupled with standard methods of peptide chemistry, e.g. HBTU/HOBt (step b). The steps a and b are repeated until the completion of the peptide assembly. The introduction of the N-terminal capping group can be achieved by standard acylation methods (step e). The C-terminal peptide N-ethylamide is cleaved from the polymer by reaction with acids e.g. trifluoroacetic acid.

This synthesis method allows the variation of the R-groups R1, R3, R4, R5, R6, and R7 of formula (I) by application of the respective amino acids or carboxylic acids.

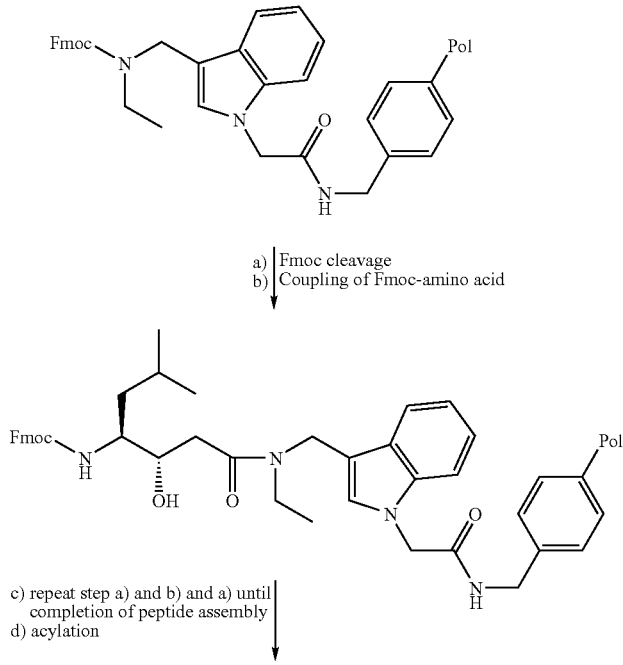

Scheme A

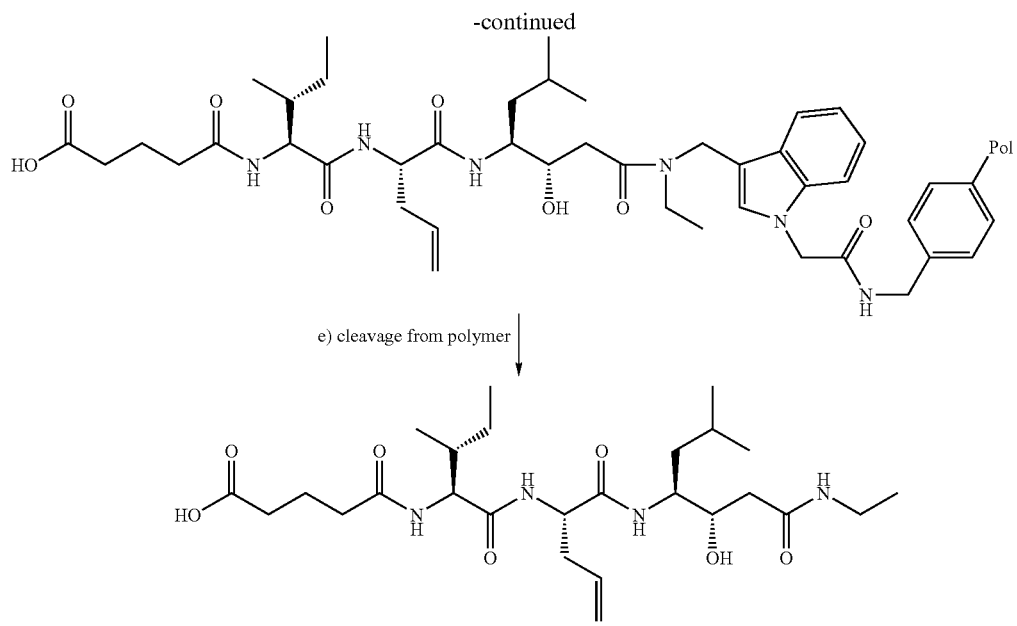

e) cleavage from polymer

Scheme B illustrates the synthesis of peptides with variations of the C-terminal amide part. A protected peptide fragment is first synthesized by standard solid phase peptide synthesis on solid support. After cleavage of the peptide the C-terminal amidation reaction is carried out by standard acylation methods in solution phase. In case that the amine contains additional functional groups these need to be protected before the acylation and deprotected afterwards. Suitable protecting groups are tert.-butyloxycarbonyl for amines, tBu-ester for acids or tBu-ether for phenols.

This method allows the variation of R2 in formula (I) by application of different amines in the last acylation step and the variation of R1, R3, R4, R5, R6, and R7 by application of the respective amino acids or carboxylic acids.

Scheme B

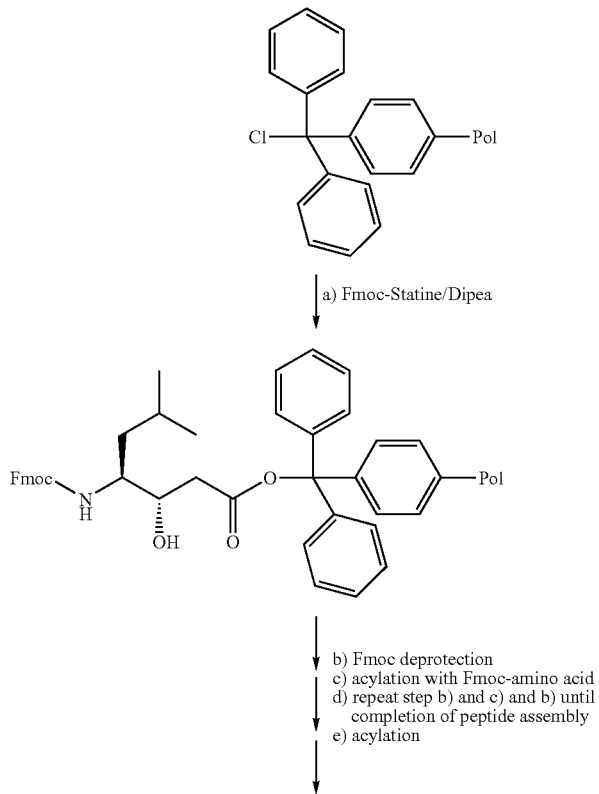

a) Fmoc-Statine/Dipea b) Fmoc deprotection
c) acylation with Fmoc-amino acid
d) repeat step b) and c) and b) until completion of peptide assembly
e) acylation

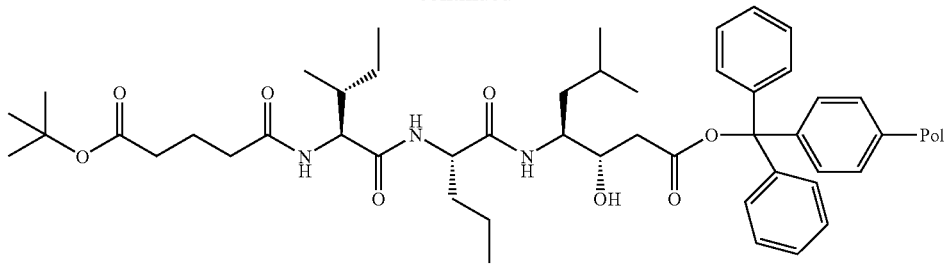

f) cleavage from polymer

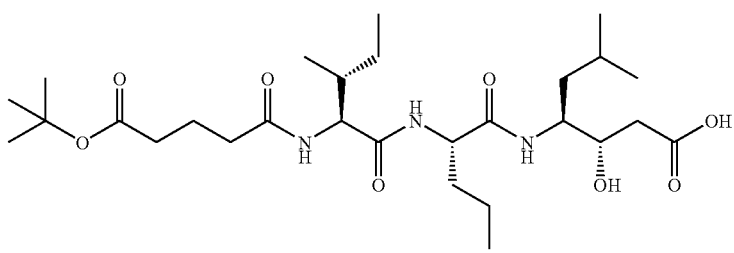

g) acylation with amine
h) deprotection

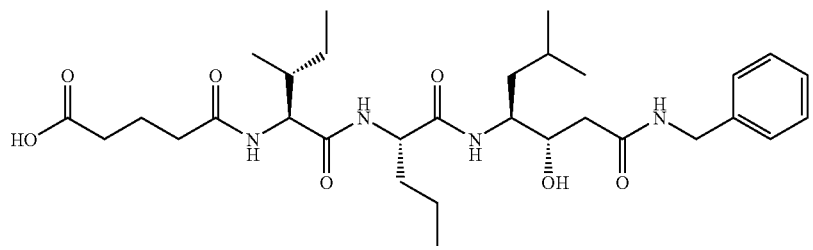

The central core of the compounds of the invention is a statine derivative. Necessary starting materials being statine derivatives optionally bearing a suitable protection group are commercially available from different vendors like Bachem (CA, US; EMD Biosciences (CA, US); Neosystems (California, US) or Advanced ChemTech (KY, US). In cases where the statine derivative is not commercially available it can be prepared by well known literature procedures or according to the scheme C:

Scheme C

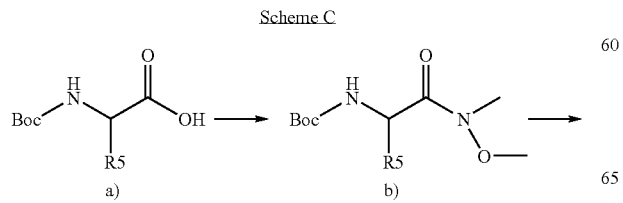

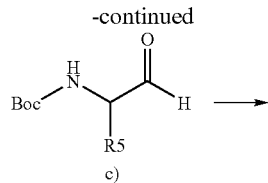

c)

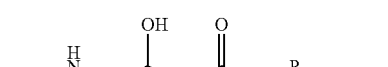

d)

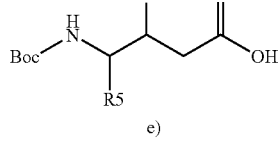

e)

Starting from the Boc-protected aminoacid a) the Weinreb amide b) is prepared using dimethylhydroxylamine using standard peptide coupling conditions, in particular TBTU/DIPEA. The product is then reduced to the amino acid aldehyde c) using LiALH₄. The Boc-protected statine derivative d) is synthesized from aldehyde c) by condensation with ethylacetate in the presence of LDA. If desired, diasteromers could be separated at this stage by chromatography. After this the Boc-protected statine e) is liberated from the ester by the treatment with sodium hydroxide in ethanol.

The final products were assembled according to the general scheme D:

Scheme D

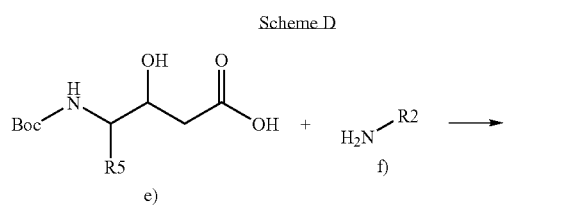

e)        f)

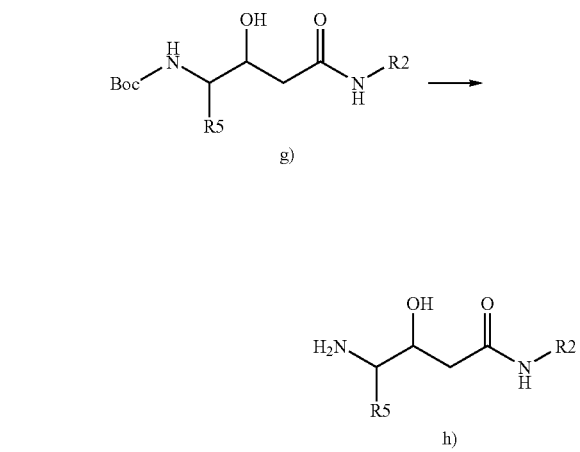

g)

h)

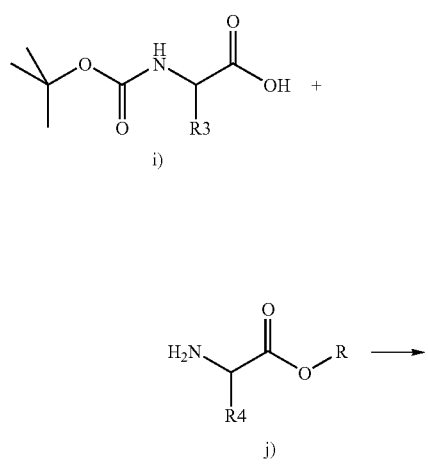

i)

j)

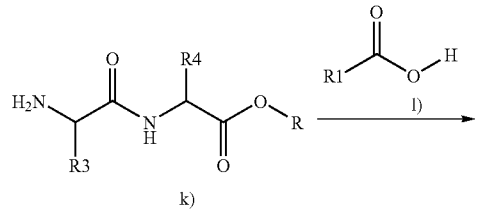

k)

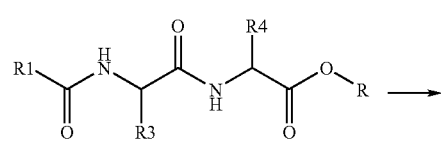

m)

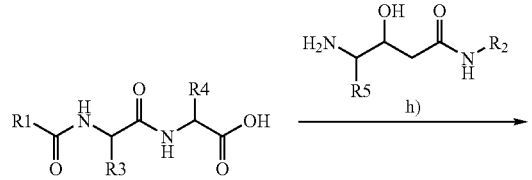

n)

o)

Coupling of the acid e) (scheme C) with the amine f) using standard coupling conditions, in particular using TBTU/DIPEA, gave intermediate g). The boc-protected statine derivative g) was deprotected with TFA to yield h).

The amine of the compound h) was coupled with the next building block n) which was synthesized as follows:

Coupling the appropriate N-terminal boc-protected amino acid i) with the appropriate C-terminal amino acid ester j) under standard coupling conditions, in particular using TBTU/DIPEA, and subsequent TFA Boc-deprotection delivered the dipetpide ester k). This was coupled under standard coupling conditions, in particular using TBTU/DIPEA, with the N-terminal acid i) which could bear a suitable protection group if neccessary to yield the intermediate ester m) which was in turn saponified with sodium hydroxide to deliver the building block n) as the acid.

Coupling of the acid n) with the statine amine h) using standard coupling conditions, in particular using TBTU/DIPEA, gave the final product o) after a deprotection step if neccessary.

Compounds of the invention that are substituted with fluor in the statine core can be synthesized according to scheme C and scheme D or by solid phase synthesis outlined in scheme A and scheme B. The necessary fluorinated statine r) was prepared as follows:

Scheme E

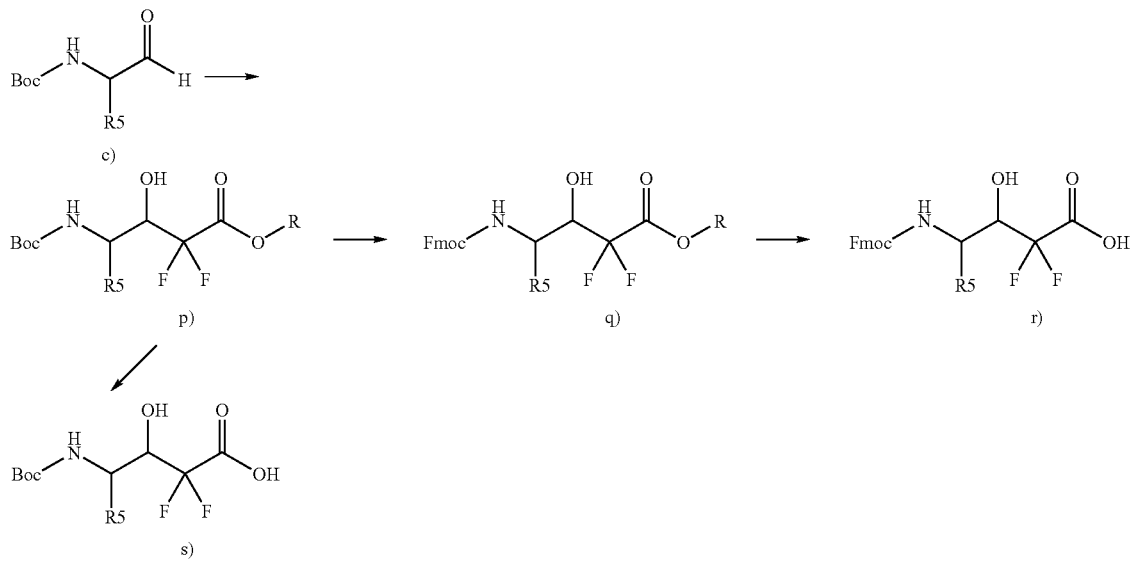

According to scheme E the amino acid aldehyde c) (scheme C) which was synthesized from the corresponding Weinreb amide or by oxidation of the corresponding amino acid alcohol using eg. Swern conditions or Dees/Martin reagent, was reacted with ethylbromo-difluoroacetate in the presence of zinc powder to yield the ester p). The boc-protected ester p) was saponified to give the acid s) which was used in solution phase chemistry according to schemes C and D.

Unless defined otherwise, all scientific and technical terms used herein have the same meaning as commonly understood by one of skill in the art to which this invention belongs. All patents and publications referred to herein are hereby incorporated by reference for all purposes. The definitions and explanations below are for the terms as used throughout this entire document including both the specification and the claims.

All temperatures are in degrees Celsius, $(M+H)^+$ refers to the positive ion of a parent plus a hydrogen atom, BOC refers to 1,1-dimethylethoxy carbonyl or t-butoxycarbonyl, BOP refers to benzotriazol-1-yloxy-tris (dimethylamino) phosphonium hexafluoro-phosphate, Bzl refers to benzyl, CBZ refers to benzyloxycarbonyl, CDI refers to 1,1'-carbonyldiimidazole, Chromatography (column and flash chromatography) refers to purification/separation of compounds expressed as (support, eluent). It is understood that the appropriate fractions are pooled and concentrated to give the desired compound (s), CMR refers to C-13 magnetic resonance spectroscopy, chemical shifts are reported in ppm (8) downfield from TMS, Cpa refers to cyclopropyl alanine, DIC refers to dicyclohexyl carbodiimide, DIPAMP refers to (R,R)-1,2-Ethanediylbis[(2-methoxyphenyl)phenylphosphine]

DCC refers to N,N'-dicyclohexylcarbodiimide

DCM refers to dichloromethane,

Dipea refers to diisopropylethylamine,

DIPEA refers to diisopropylethylamine,

DMAP refers to 4-dimethylaminopyridine,

DMF refers to dimethylformamide,

EDC refers to ethyl-1-(3-dimethylaminopropyl) carbodiimide or 1-(3-dimethylamino-propyl)-3-etliylcarbodiimide hydrochloride, EI refers to electron impact. CI refers to chemical ionization. FAB refers to fast atom bombardment, Ether refers to diethyl ether, unless specified otherwise, FMOC refers to 9-fluorenylmethyl carbonate, Gly(Allyl) refers to allylglycine HATU refers to O-(7-azabenzotriazol-1-yl)-N,N,N',N'-tetramethyluronium hexafluoro-phosphate, HBTU refers to 2-(1H-Benzotriazole-1-yl)-1,1,3,3-tetramethyluronium hexafluoro-phosphate, HOAc refers to acetic acid, HOAT refers to 1-Hydroxy-7-azabenzo-triazole, HOBt refers to 1-hydroxy benzotriazole hydrate, HPLC-MS refers to high pressure liquid chromatography with mass detection, HRMS refers to high resolution mass spectrometry, Ile refers to isoleucine IR refers to infrared spectroscopy, MPLC refers to middle pressure liquid chromatography, MS refers to mass spectrometry expressed as m/e, m/z or mass/charge unit, NBS refers to N-bromosuccinimide, NMM refers to N-methylmorpholine, NMP refers to N-methylpyrrolidone, NMR refers to nuclear (proton) magnetic resonance spectroscopy, chemical shifts are reported in ppm (d) downfield from TMS, Nva refers to norvaline, Pol refers to polymer which is typically used for solid phase synthesis psi refers to pounds/in$^2$, RF refers to retention factor(DC Alufoil, Alugram SIL G/UV₂₅₄ Machery-Nagel, Düren, Germany), RT refers to retention time, Saline refers to an aqueous saturated sodium chloride solution, Sta refers to (3S,4S)-4-amino-3-hydroxy-6-methyl-heptanoic acid, TBTU refers to 1-[Bis(dimethylamino)methylen]-1-H-benzotriazolim-tetrafluoroborate-3-oxide, tBu refers to tert.-butyl, TFA refers to trifluoracetic acid, THF refers to tetrahydrofurane, TMOF refers to trimethylorthoformate, Val refers to valine.

H II mobile phase for thin-layer-chromatography consisting of:

| | |
|---|---|
| 360 ml | n-Butanol |
| 150 ml | water |
| 150 ml | formic acid |
| 150 ml | aceton |
| 50 ml | dichloromethane |

EXAMPLES

Without further elaboration, it is believed that one skilled in the art can, using the preceding description, practice the present invention to its fullest extent.

The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

The products were analyzed by analytical HPLC-MS and/or NMR.

HPLC-conditions 1: Column: Grom Nucleosil C18 250×2 mm, 5 µm; Flowrate: 0.3 ml/min; Buffer A: 0.1% TFA; Buffer B: 0.1% TFA in MeCN; Gradient: linear from 10% B to 100% B in 30 min;

HPLC-conditions 2: Column: Waters X-Terra 4.6×50 mm, 3.6 µm; Flowrate: 1 ml/min; Buffer A: 0.1% TFA; Buffer B: 0.08% TFA in MeCN; Gradient: linear from 95% A to 2% A in 5 min;

HPLC-conditions 3: Column: XTerra MS C18 4.6×30 mm, 2.5 µm; Flowrate 1 ml/min.; Gradient: water:acetonitrile 95:5 to 2:98 in 4.5 minutes.

HPLC-conditions 4: Waters ZMD, Alliance 2695 HPLC, Waters 2700 Autosampler, Waters 996 diode arraydetector, column Varian, Microsorb 100 C₁₈ 3 µm, 4.6 mm×50 mm, batch no. 2231108 (column-temperature: constantly at 25° C.). A: water with 0.13% TFA, B: acetonitrile with 0.10% TFA; Gradient: A:B 95:5 to 2:98 in 5.7 minutes, detection at 210–500 nm.

HPLC-MS (method: fast): Waters Alliance 2690 HPLC, Waters 2700 Autosampler, Waters 996 diodearray detector; column: waters, Xterra MS C18 2.5 µm, 4.6 mm×30 mm, (column-temperature: constantly at 25° C.).A: water with 0.10% TFA, B: acetonitril with 0.08% TFA, Gradient: A:B 95:5 to 2:98 in 4.5 minutes, detection at 210–500 nm Synthesis of Example 1

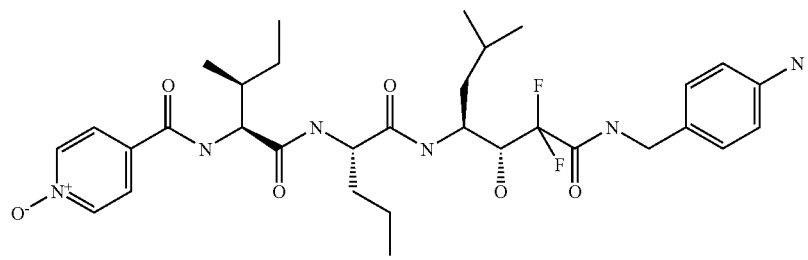

a) Preparation of 1-a:

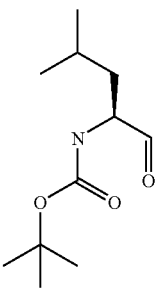

1-a 5.0 g (18.2 mmol) N-(tert.-butoxycarbonal)-L-leucin-N-methoxy-N-methylamide (Weinreb amide) in 40 ml THF were added slowly to a suspension of 700 mg (18.4 mmol) LiAlH₄, in 40 ml THF at −35° C. under nitrogen and stirred for 1.5 hours. Then 1.8 ml saturated diammoniumtartrate solution and Na₂SO₄ were added and the resulting suspension was stirred for 30 minutes, filtered over a short plug of silica gel and concentrated to yield 1-a, which was used in the next step without further purification and storage.

RF=0.6 (silica gel, petrolether: ethylacetate=2:1, color with iodine)

b) Preparation of 1-b:

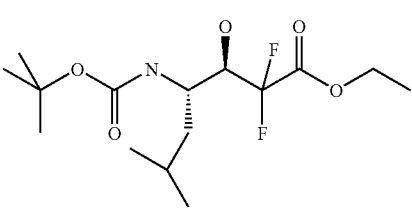

1-b

100 μl (0.76 mmol) Ethylbromodifluoroacetate were added slowly to a suspension of 3.1 g (47.4 mmol) zinc powder in 50 ml THF at 70° C. under nitrogen and stirred for 1 minute, after that a solution consisting of 5.9 ml (45.10 mmol) ethylbromodifluoroacetate and 3.8 g (17.7 mmol) 1-a in 50 ml THF were added slowly. The resulting suspension was stirred for 1 hour under reflux. At room temperature the reaction was diluted with dichloromethane and 5% NaHSO₄ solution. The organic phase was separated, dried and evaporated. The residue was purified by MPLC (silica gel, petrolether/ethylacetate=5:1 to 4:1) to yield 1.4 g (23%) 1-b as a yellow oil.

RF=0.5 (silica gel, petrolether: ethylacetate=2:1, ninhydrin spray)

ES-MS (M+H)⁺340 c) Preparation of 1-c:

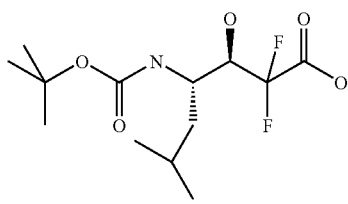

1-c 1.3 g (3.8 mmol) 1-b in 25 ml ethanol and 3 ml water were treated with 600 mg (25.1 mmol) LiOH and stirred at room temperature for 4 hours. Ethanol was distilled off and the residue was diluted with water and ethylacetate. The mixture was brought to pH 6 with 5% NaHSO₄ solution. The organic phase was separated, dried and concentrated to yield 1.1 g (92%) 1-c.

RF=0.7 (silica gel, H II, ninhydrin spray)

d) Preparation of 1-d:

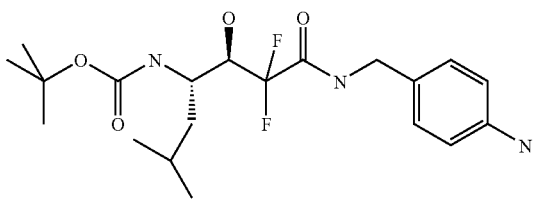

1-d 500 mg (1.61 mmol) 1-c, 185 μl (1.62 mmol) 4-Aminomethylphenylamine were dissolved in 20 ml THF, 550 μl (3.16 mmol) DIPEA, 550 mg (1.71 mmol) TBTU and 220 mg (1.63 mmol) HOBT were added and the mixture was stirred at room temperature over night. The mixture was evaporated and extracted with ethylacetate and saturated bicarbonate solution. The combined organic phases were concentrated. The addition of diethylether led to crystallisation of 220 mg (33%) 1-d.

RF=0.4 (silica gel, dichloromethane:methanol=9:1)

ES-MS (M+H)⁺416 e) Preparation of 1-e:

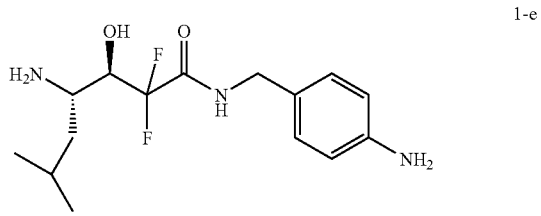

1-e 220 mg (0.53 mmol) 1-d were dissolved in 10 ml dichloromethane. The mixture was cooled to 0° C. and 450 μl (5.78 mmol) TFA were added. After warming to room temperature the reaction was stirred over night. The mixture was concentrated, diluted with water and ethylacetate. Under ice cooling the mixture was adjusted to basic pH with NH₃. The organic phase was separated, dried and evaporated to yield 110 mg (66%) of 1-e as a white solid.

RF=0.1 (silica gel, dichloromethane:methanol=9:1, ninhydrin spray)

ES-MS (M+H)⁺316 f) Preparation of 1-f:

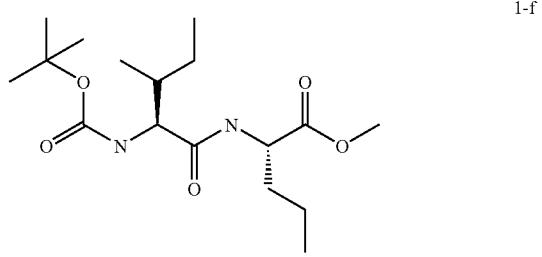

1-f 11.6 g (50.0 mmol) N-tert-butoxycarbonyl-L-isoleucine, 16.1 g (50.0 mmol) TBTU and 25.5 ml (150 mmol) DIPEA were dissolved in 230 ml THF. 8.4 g (50.0 mmol) L-2-aminovalericacid-methylester-hydrochloride were added and the reaction was stirred at room temperature overnight. The mixture was extracted with 20% KHSO₄ solution and water. The organic phase was separated with an isolute phase separator and evaporated. The residue was purified by MPLC (silica gel, dichloromethane/methanol=95:5) to yield 15.9 g (92%) 1-f ES-MS (M+H)⁺345 g) Preparation of 1-g:

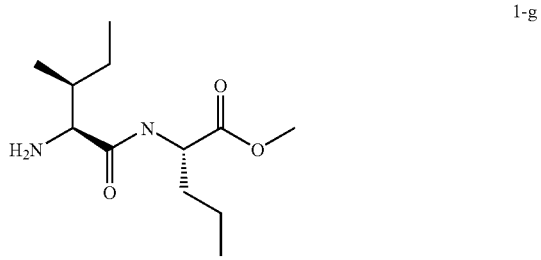

1-g 13.0 g (37.8 mmol) 1-f were dissolved in 100 ml dichloromethane and 32 ml (280.7 mmol) TFA were added under ice cooling. The reaction was stirred at room temperature overnight. The solvent was evaporated. The addition of diethylether led to crystallisation 12.4 g (91%) of the trifluoracetate of 1-g as a white solid.

RF=0.12 (silica gel, dichloromethane: methanol=95:5, ninhydrin spray)

ES-MS (M+H)⁺245 h) Preparation of 1-h:

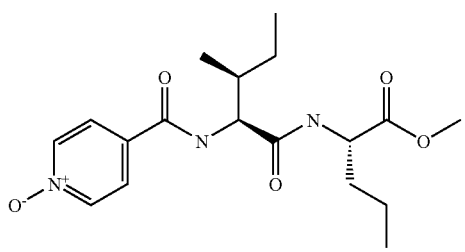

1-h Was prepared from 12.3. g (34.3 mmol) 1-g and 4.8 g (34.5 mmol) 1-oxy-isonicotinic using the standard coupling procedure analogous to the preparation of 1-f yielded 12.1 g (97%) 1-h as a yellow oil.

ES-MS (M+H)⁺366 i) Preparation of 1-i:

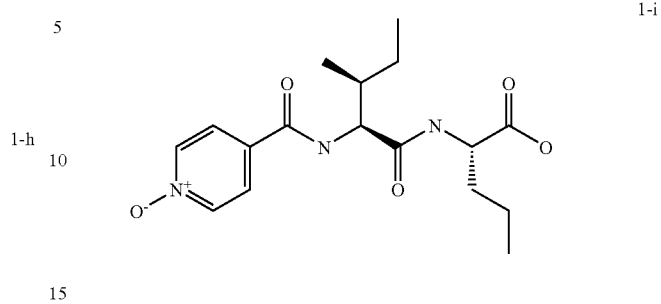

12.1. g (33.1 mmol) 1-h In 270 ml methanol were treated with 133 ml 1N NaOH and stirred at room temperature overnight. Methanol was distilled off and the residue was diluted with water and made acidic with 5N HCl under ice cooling. The precipitate was filtered off and washed with water to yield 6.7 g (58%) of 1-i.

ES-MS (M+H)⁺352 j) Preparation of 1-j:

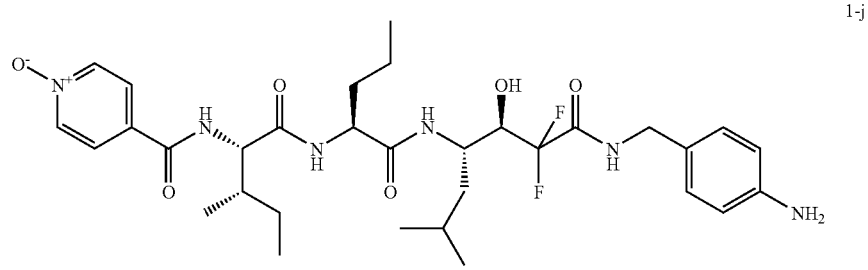

55 mg (0.16 mmol) 1-i, 32 mg (0.24 mmol) HOBt and 21 µl (0.19 mmol) NMM were dissolved in 8 ml DMF and 50 mg (0.16 mmol) 1-e were added.

The mixture was cooled to −30° C. and 40 µl (0.23 mmol) EDC was added. The reaction was allowed to warm up to −20° C. in 2 hours and stirred for another 1,5 hours at this temperature. Then the reaction was allowed to warm up to room temperature within 3 hours and stirred over night. The reaction mixture was concentrated. The addition of water led to crystallisation of 50 mg (49%) 1-j as a lightbrown solid.

ES-MS (M+H)⁺649

Synthesis of Example 2

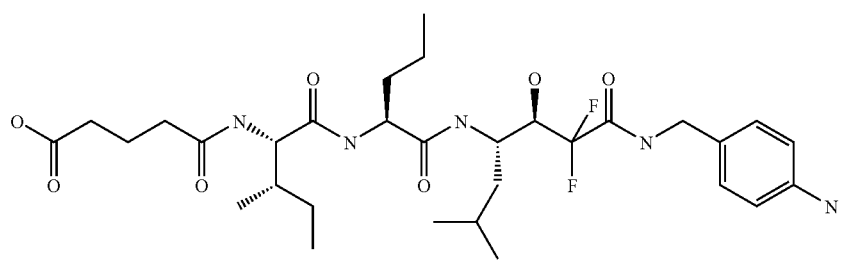

a) Preparation of 2-a:

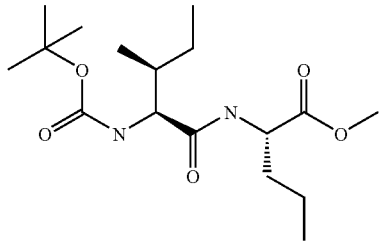
2-a 2-a was prepared from 13.8 g (59.7 mmol) N-tert-butoxy-carbonyl-L-isoleucine and 10.0 g (59.7 mmol) L-2-aminovalericacid-methylester-hydrochloride using a standard coupling procedure analogous to the preparation of 1-f to yield 20.1 g (98%) 2-a as a white solid.

ES-MS (M+H)$^+$344 b) Preparation of 2-b:

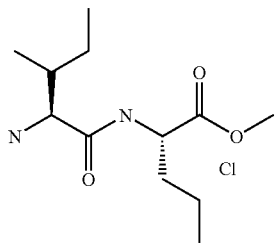
2-b 20.1 g (58.4 mmol) 2-a were dissolved in 150 ml dichloromethane and 32 ml (100 mmol) 4N HCl in dioxan were added. The reaction was stirred over night at room temperature. The mixture was evaporated to yield quantitativly 2-b as the hydrochloric acid salt.

ES-MS (M+H)$^+$245 c) Preparation of 2-c:

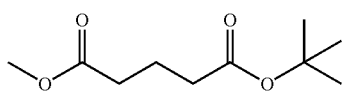
2-c 51.7 ml (97%, 400 mmol) Glutaric acid monomethylester, 90.8 g DCC (440 mmol) and 12.2 g DMAP (100 mmol) were dissolved in 150 ml tert-butanol. After 20 minutes 200 ml dichloromethane were added. The mixture was stirred for 24 hours at room temperature. The resulting slurry was filtered and the residue washed with dichloromethane. The organic phase was washed with 10% citric acid and 10% bicarbonate solution, dried and evaporated. The resulting oil was distilled to yield 65.7 g (81%) 2-c as a colourless oil. boiling point: 64° C. (4.9$^{-2}$ mbar)

ES-MS (M+H)$^+$203.2 d) Preparation of 2-d:

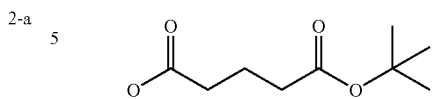
2-d 65.7 g (325 mmol) 2-c in 200 ml methanol were treated with 235 ml (970 mmol) 10% LiOH solution and stirred under ice cooling for 4 h. Using 2N HCl the reaction mixture was neutralized to a pH of 6.8. Methanol was distilled off and the aqueous residue was diluted with dichloromethane. At 0° C. the pH was brought to 3.8 with 10% citric acid. Standard work up yielded 8.9 g (15%) 2-d.

ES-(−)MS (M-H)$^-$187 e) Preparation of 2-e:

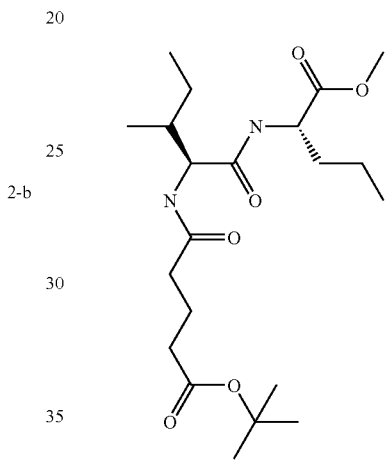
2-e 16.0 g (57.0 mmol) 2-b, 10.8 g (57.2 mmol) 2-d were dissolved in 320 ml THF, 14.9 ml (115.0 mmol) DIPEA, 18.6 g (58.0 mmol) TBTU and 7.7 g (57.0 mmol) HOBt were added and the mixture was stirred at room temperature over night. The mixture was evaporated and extracted with ethylacetate and saturated bicarbonate solution. The combined organic phases were concentrated. The residue was purified by MPLC (silica gel, cyclohexane/ethylacetate=7:3) to yield 14.2 g (60%) of 2-e.

ES-MS (M+H)$^+$415 f) Preparation of 2-f:

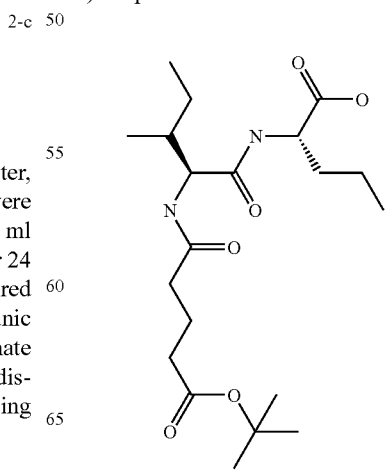
2-f 4.8 g (90%, 10.5 mmol) 2-e ml ethanol were treated with 10.0 ml (36.3 mmol) 10% LiOH solution and stirred at room temperature for 2 hours. Using 4N HCl the reaction mixture was neutralized to a pH of 7.0 under ice cooling. Ethanol was distilled off and the aqueous residue was diluted with water and ethylacetate. At 0° C. the pH was brought to 3.5 with 10% citric acid. After standard work up the residue was purified by MPLC (silica gel, dichloromethane/ethanol=100:0 to 85:15) to yield 3.3 g (78%) of 2-f.

RT=2.9 min (HPLS-MS)
ES-MS (M+H)⁺401 g) Preparation of 2-g

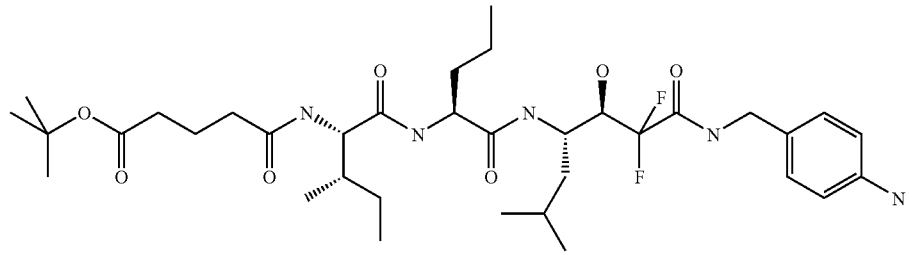

2-g

In analogy to the preparation of 1-j 88 mg (0.22 mmol) 2-f and 70 mg (0.22 mmol) 1-e yielded 140 mg (91%) 2-g as white solid.

RT=2.83 min (HPLC-MS)
ES-MS (M+H)⁺698 h) Preparation of 2-h:

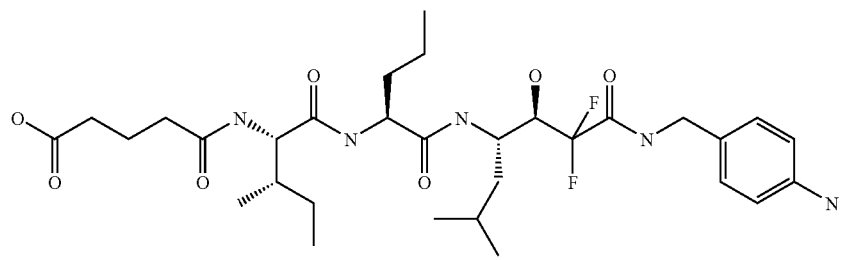

2-h 140 mg (0.20 mmol) 2-g were dissolved in 10 ml dichloromethane. The mixture was cooled to 0° C. and 500 μl (6.43 mmol) TFA were added. After warming to room temperature the reaction was stirred over night. The mixture was evaporated and diluted with water and dichloromethane. Under ice cooling the mixture first was adjusted to basic pH with NH₃ and then neutralized with saturated NaHSO₄ solution. The solid was filtered and dried to yield 5.8 mg (5%) of 2-h as a lightbrown solid.

RT=2.42 min (HPLC-MS)
ES-MS (M+H)⁺642

Synthesis of Example 3

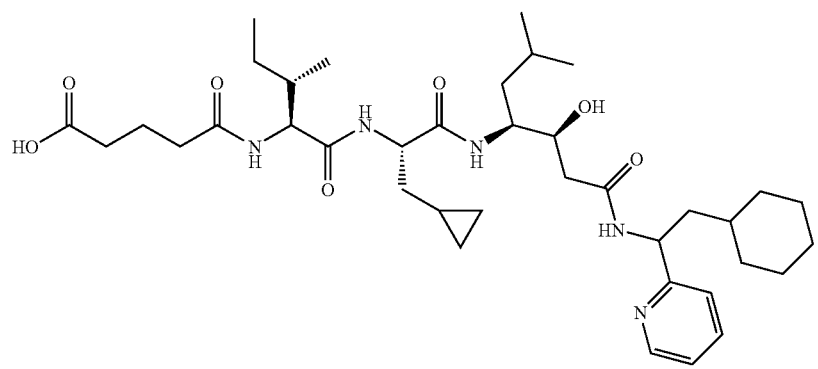

a) Preparation of 3-a:

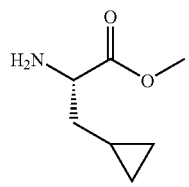
3-a 4.6 g (20.0 mmol) Boc-beta-cyclopropyl-ala-OH were dissolved in 50 ml methanol. At 20° C. 1.5 ml (20.0 mmol) thionylchloride were added slowly. The reaction was stirred for 1 day. The reaction mixture was concentrated and the addition of diethylether led to crystallisation of 2.4 g (59%) 3-a as the hydrochoric acid salt.

b) Preparation of 3-b:

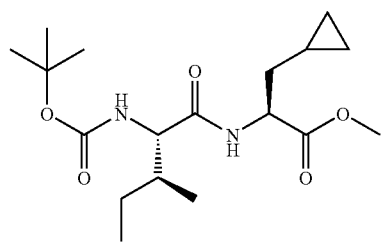
3-b

In analogy to the preparation of 1-f 3.0 g (13.0 mmol) N-Boc-L-isoleucine and 2.3 g (13.0 mmol) 3-a yielded 3.9 g (84%) 3-b.
ES-MS (M+H)$^+$357 c) Preparation of 3-c:

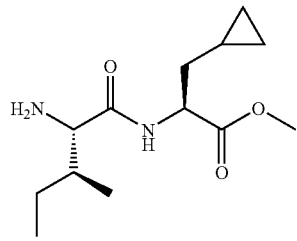
3-c

In analogy to the preparation of 1-g 3.6 g (10.0 mmol) 3-b yielded 3.4 g (90%) 3-c as the trifluoroactic acid salt.
ES-MS (M+H)$^+$257 d) Preparation of 3-d:

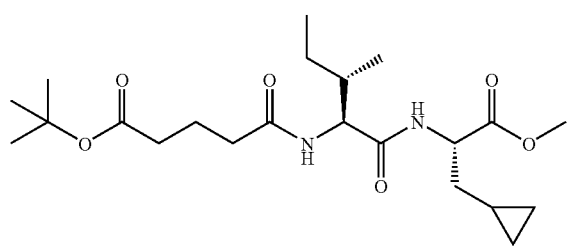
3-d

In analogy to the preparation of 2-e 1.7 g (9.0 mmol) 2-d and 3.3 g (9.0 mmol) 3-c yielded 4.4 g (97%) 3-d.
ES-MS (M+H)$^+$427 e) Preparation of 3-e:

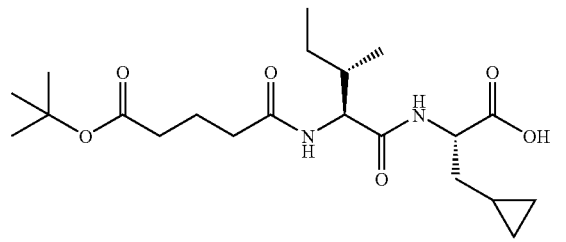
3-e 3.3 g (85%, 6.5 mmol) 3-d in 40 ml ethanol were treated with 6 ml 2N NaOH and stirred at room temperature for 3 h. Using 2N HCl the reaction mixture was neutralized to a pH of 6–7. Ethanol was distilled off and the aqueous residue was brought to pH 3.0 with 10% citric acid under ice cooling. The crashed out solid was filtered off and washed with diethylether to yield
2.7 g (96%) 3-e.
ES-(–)MS (M-H)-411 f) Preparation of 3-f:

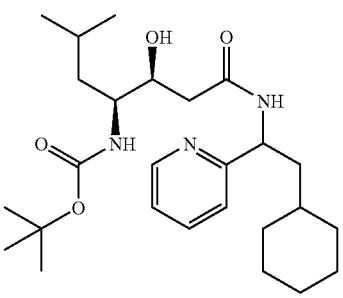
3-f

In analogy to the preparation of 1-d 300 mg (1.09 mmol) Boc-Statine-OH (4-(Boc-amino)-3-hydroxy-6-methyl-heptanoic acid) and 223 mg (1.09 mmol) 2-cyclohexyl-1-pyridin-2-yl-ethylamine yielded 400 mg (80%) 3-f.
ES-MS (M+H)$^+$427 g) Preparation of 3-g:

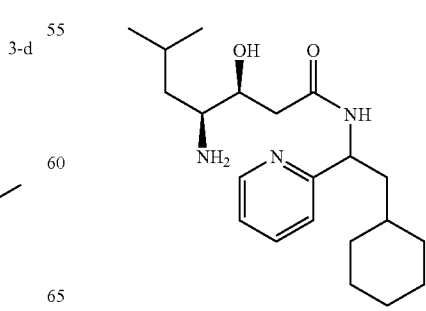
3-g 360 mg (0.78 mmol) 3-f were dissolved in 5 ml dichloromethane and 500 µl (6.5 mmol) TFA were added. The reaction was stirred at room temperature for 2 hours. The mixture was evaporated and the residue was diluted with dichloromethane and extracted with 20% KHCO₃ solution and water. The organic phase was separated with an isolute phase separator and evaporated to yield 360 mg (97%) of 3-g as a yellow oil of the trifluoroacetic acid salt.

ES-MS (M+H)⁺361 h) Preparation of 3-h:

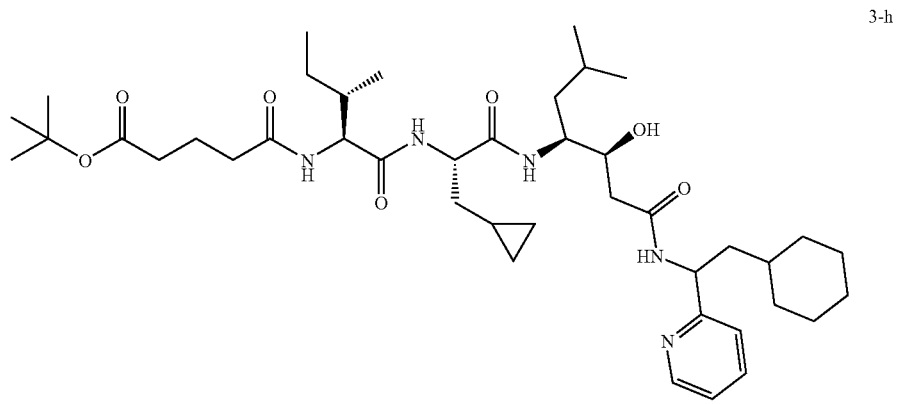

3-h 3-h was prepared from 312 mg (0.76 mmol) 3-e and 360 mg (0.76 mmol) 3-g using a standard coupling procedure analogous to the preparation of 1-f and yielded 100 mg (11%) 3-h as a yellow oil.

RT=3.25 (HPLC-MS)

i) Preparation of 3-i:

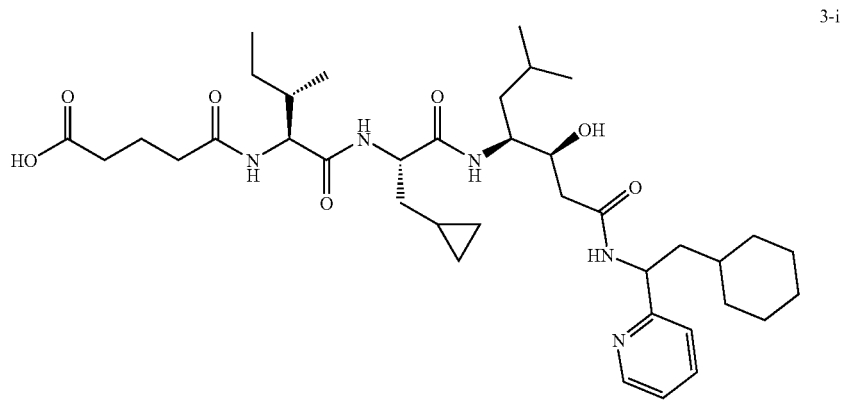

3-i 40 mg (0.05 mmol) 3-h were dissolved in 10 ml dichloromethane and 500 μl (6.5 mmol) TFA were added. The reaction was stirred at room temperature for 2 hours. The mixture was diluted with water and separated. The organic phase was extracted with 1 N NaOH and separated with an isolute phase separator. The water phase was made acidic with 1 N HCl and the crashed out crystals were filtered and dried to yield 10 mg (26%) of 3-i as a hydrochloric acid salt as a white solid.

ES-MS (M+H)⁺700

Synthesis of Example 4

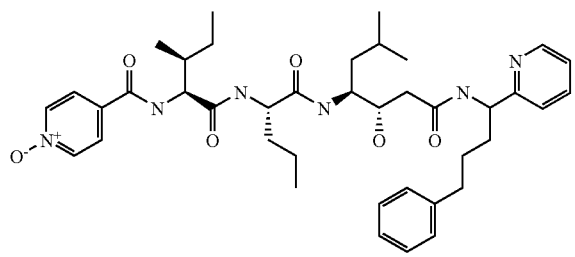

a) Preparation of 4-a:

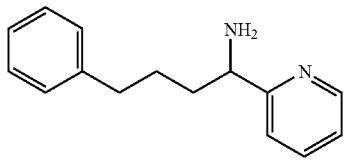

6.3 ml (41.5 mmol) 1-Bromo-3-phenylpropane were dissolved in 50 ml diethylether and added slowly to 1.0 g (41.1 mmol) magnesium turnings. The mixture was warmed until the reaction started. Then the rest of the solution was added while allowing reflux. After that the mixture was stirred for 1 hour under reflux. At 0° C. the solution of 3.0 g (28.8 mmol) 2-cyanopyridine in 50 ml diethylether was added slowly keeping the temperature under 10° C. Then the mixture was stirred for 1 hour under ice cooling. 100 ml methanol were added, and the reaction was stirred for 45 minutes under ice cooling. 2.3 g (60.8 mmol) NaBH₄ were added in little portions keeping the temperature under 10° C. The mixture was stirred for 2 hours at room temperature and then evaporated. The residue was diluted with water and 2N HCl and extracted with dichloromethane. The water phase was adjusted to basic pH with 2N NaOH and extracted with dichloromethane, separated with an isolute phase separator and concentrated. The residue was dissolved in diethylether and a solution of HCl in diethylether was added. The crashed out crystals were filtered and dried to yield 2.7 g (25%) 4-a as lightbrown crystals of the hydrochloric acid salt.

ES-MS (M+H)⁺227 b) Preparation of 4-b:

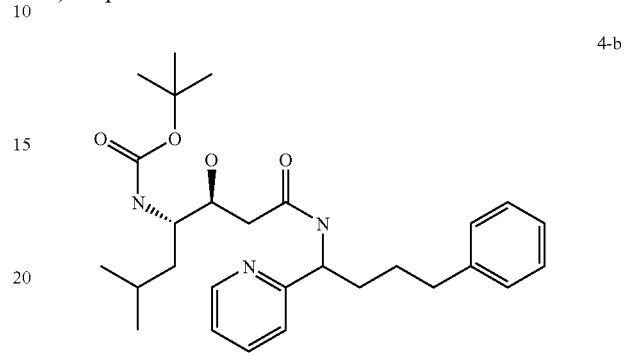

4-b was prepared from 300 mg (1.1 mmol) BOC-Statine-OH (4-(Boc-amino)-3-hydroxy-6-methyl-heptanoic acid) and 250 mg (1.1 mmol) 4-a using a standard coupling procedure analogous to the preparation of 1-f to yield 400 mg (76%) of 4-b as a yellow oil.

RT=2.85 min (HPLC-MS, method fast)

c) Preparation of 4-c:

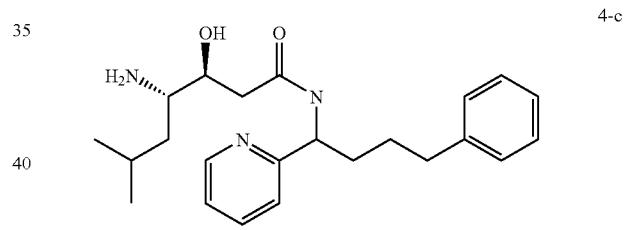

400 mg (0.83 mmol) 4-b were dissolved in 5 ml dichloromethane and 1 ml TFA were added. The reaction was stirred at room temperature for 3 hours and concentrated. The residue was purified by MPLC (silica gel, dichloromethane/methanol=9:1) to yield 380 mg (92%) of 4-c as the trifluoroacetic acid salt as a yellow oil.

ES-MS (M+H)⁺384 d) Preparation of 4-d:

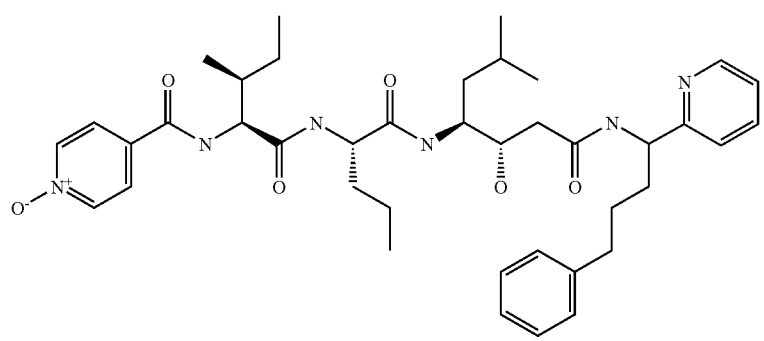

4-d was prepared from 130 mg (0.37 mmol) 1-i and 185.0 mg (0.37 mmol) 4-c using a standard coupling procedure analogous to the preparation of 1-f to yield 250 mg (94%) 4-d as a lightyellow solid.

ES-MS (M+H)$^+$ 717

The examples 5, 6, 7, 10, 11, 20, 24, 25, 33, 37 were synthesized in anology to example 3. The example 17 was synthesized in anology to example 4. The example 15 was synthesized in anology to Example 4; the carboxylic acid was liberated from the ester at the last step. The compounds 5, 6, 7, 10, 11, 15, 17, 20, 24, 25, 33, 37 gave the yields, appearance and physical data listed in the following table:

| Example # | Structure | YIELD % | appearance | RT | (M + H)+ |
|---|---|---|---|---|---|
| 5 | Chiral 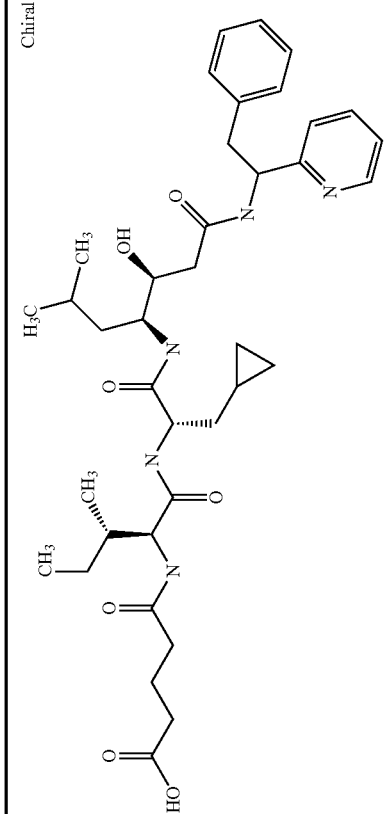 | 87 | white crystals | | 694 |
| 6 | Chiral 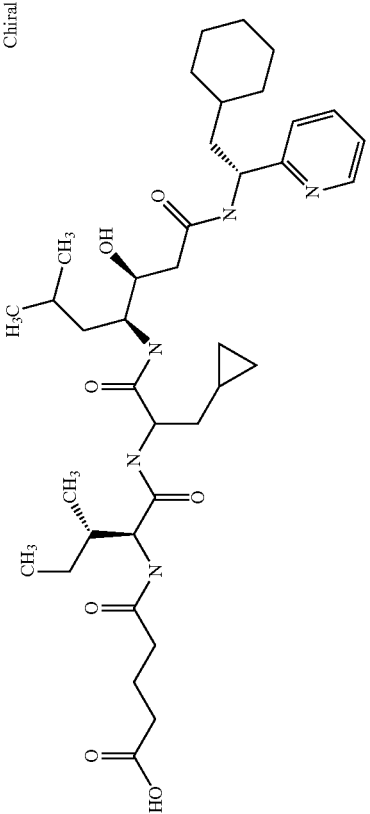 | 98 | white crystals | HPLC-MS (method: fast): 2.62/2.77 min | 700 |

-continued
| Example # | Structure | YIELD % | appearance | RT | (M + H)+ |
|---|---|---|---|---|---|
| 7 | Chiral 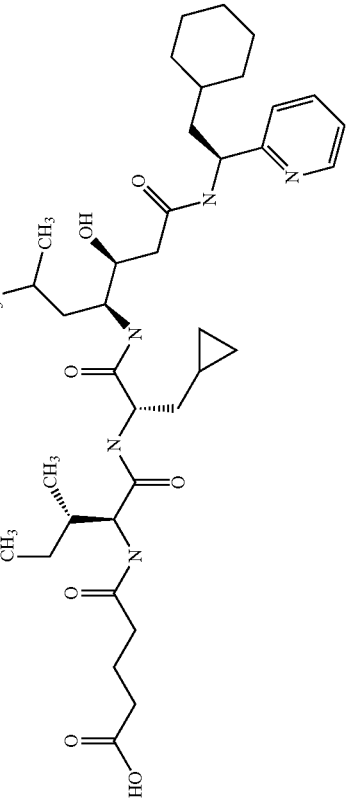 | 36 | white crystals |  | 700 |
| 10 | Chiral 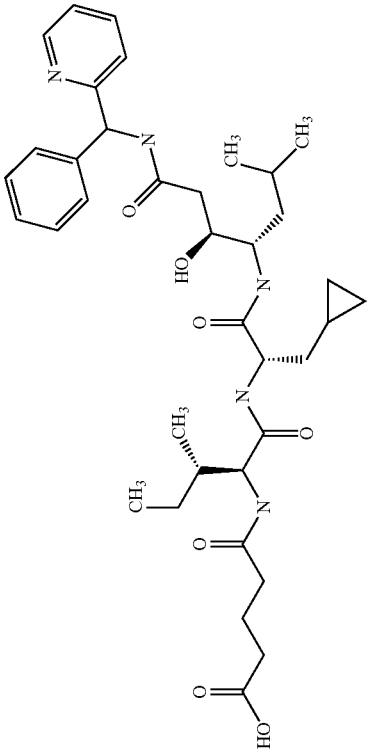 | 97 | white crystals |  | 680 |

-continued

| Example # | Structure | YIELD % | appearance | RT | (M + H)+ |
|---|---|---|---|---|---|
| 11 | Chiral | 32 | crystals | HPLC-MS (method: fast): 2.57 | 658 |
| 15 | Chiral | 21 | | HPLC conditions 4: 3.8 min | 642 |
| 17 | Chiral | 99 | white crystals | | 698 |

| Example # | Structure | | YIELD % | appearance | RT | (M + H)+ |
|---|---|---|---|---|---|---|
| | | Chiral | | | | |
| 20 | 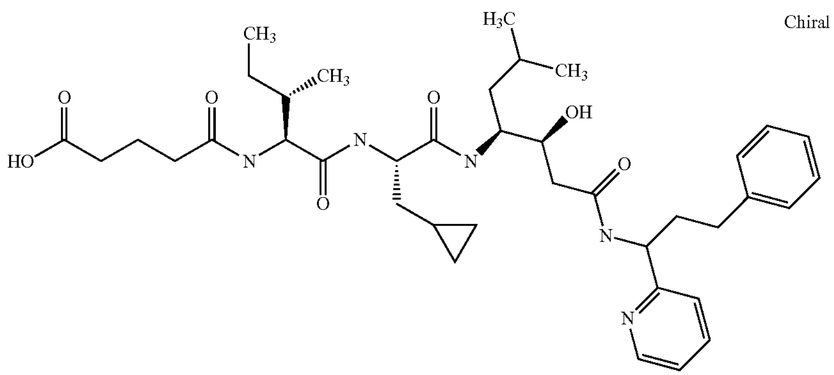 | | 27 | white crystals | | 708 |
| | | Chiral | | | | |
| 24 | 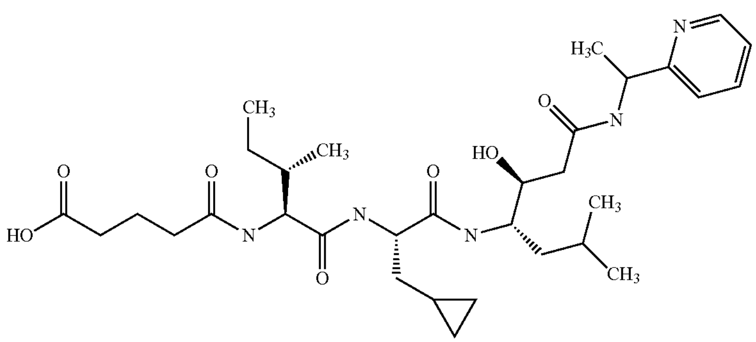 | | 50 | yellow oil | | 618 |

-continued

| Example # | Structure | YIELD % | appearance | RT | (M + H)+ |
|---|---|---|---|---|---|
| 25 | Chiral | 55 | crystals | | 646 |
| 33 | Chiral | 98 | white crystals | | 604 |
| 37 | Chiral | 32 | brown crystals | | 676 |

Synthesis of glutaryl-Ile-Gly(Allyl)-Sta-NHEt (Example 27)

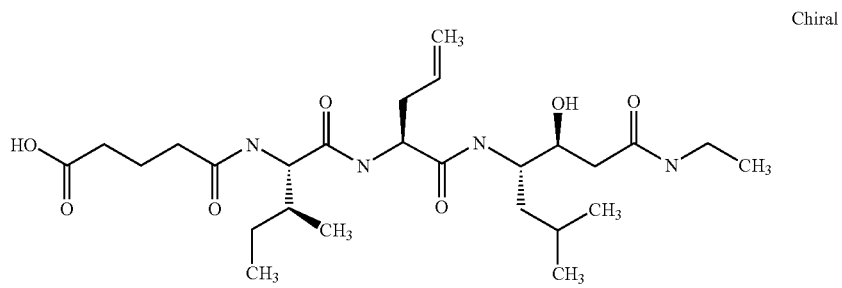

The peptide synthesis was performed on an Applied Biosystems peptide synthesizer ABI 433A using the pre-installed method FastMoc 0.25 Ω MonPrevPK.

3-((Ethyl-fmoc-amino)-methyl)-1-indol-1yl-acetyl AM resin (Novabiochem, loading 0.87 mmol/g) (287.4 mg; 0.25 mmol) was added to the reaction vessel (41 ml) and DCM (5 ml) was added to swell the resin for 6 minutes under agitation. The DCM was removed and the resin was washed with NMP (five times; 5 ml). The deprotection of the Fmoc-group was performed by treatment of the resin with 22% piperidine/DMF for 2 and 7 minutes followed by washing the resin with NMP (12 times; 5 ml).

For the coupling of the amino acids NMP (2 ml), HBTU/HOBt in DMF (2 ml, 0.45 M, 0.9 mmol) and Dipea in DMF (1 ml; 2 M) were added to the amino acid cartridges (in case of example 27 Fmoc-Sta-OH (397 mg; 1 mmol)). The amino acid was dissolved by mixing for 6 minutes. This solution was added to the resin and the reaction vessel was agitated for 2 hours. After completion of the coupling the reaction mixture was filtrated and resin was washed with NMP (12 times; 5 ml). The other amino acids Fmoc-Gly(Allyl)-OH and Fmoc-Ile-OH were incorporated in the same manner.

After completion of the peptide assembly the terminal Fmoc-group was deprotected as described above. The resin was transferred into a 10 ml syringe equipped with a filter and a solution of glutaric anhydride (114.1 mg; 0.1 mmol), Dipea (513.7 μl; 3 mmol) and DMF (3 ml) was added. The suspension was agitated for two hours. The resin was washed with DMF (5 times; 5 ml) and DCM (5 times; 5 ml) by hand. The resin was treated with a solution of 95% TFA/water (5 ml). After 30 minutes the solution was filtrated and the resin was washed with DCM (2 times, 3 ml). The combined solutions were evaporated under reduced pressure and the resulting oil was treated with diethyl ether to precipitate the peptide. The crude peptide was purified by preparative reversed phase HPLC applying an acetonitrile/water gradient. The product gave satisfactory analytical data. ES-MS: m/z=527.6 ([M+H]+)

Example 22 was synthesized analogously by variation of the amino acids or the capping groups. In case of acylations with carboxylic acids the acid (4 eq.) was activated with HATU (4 eq.), HOAt (4 eq.) in presence of Dipea (4 eq.) in DMF.

Synthesis of glutaryl-Ile-Nva-Sta-NHBzl (Example 21)

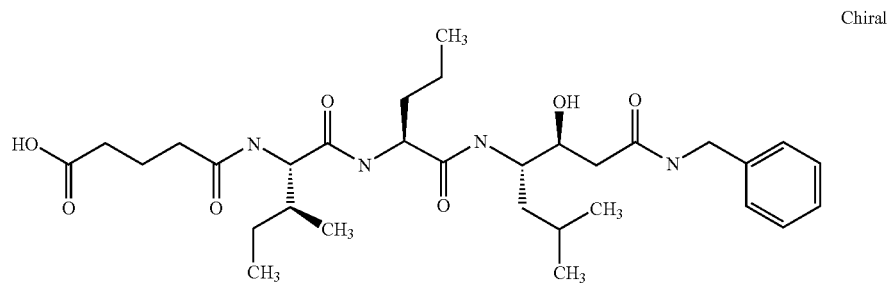

The synthesis of example 21 involves the preparation of a protected peptide fragment on solid phase and afterwards an acylation at the C-terminus in solution phase (see scheme B)

The protected peptide fragment was synthesized by solid phase synthesis on a commercially available chlorotrityl-polystyrene resin (TCP resin, PepChem NMI TT GmbH)(10 g, 14 mmol). The first amino acid Fmoc-Statine (5.7 g, 28 mmol) was dissolved in dichloromethane (50 ml) and Dipea (15 ml) and was added to the resin. The suspension was shaken for 2 hours and methanol (20 ml) was added. After additional 20 minutes of agitation the resin was filtered and washed with dichloromethane (10×) and DMF (5×).

Fmoc deprotections were performed by treatment of the resin with 30% piperidine in DMF for 2 and 20 minutes followed by washing the resin with DMF (10×). The acylation reactions were effected by treatment of the resin with a solution of TBTU (4 equiv.), HOBT (4 equiv.), Dipea (12 equiv.) and the corresponding Fmoc-amino acid or carboxylic acid (4 equiv.) in DMF at a concentration of 0.5 mol/l. In case of example 21 Fmoc-Nva, Fmoc-Ile and glutaric acid mono-tert.-butylester were coupled according to the peptide sequence.

After completion of the peptide assembly the resin was treated with a solution of 30% hexafluoroisopropanol in dichloromethane (50 ml) for 3 hours. The resin was filtered, washed with dichloromethane and the filtrate was evaporated under reduced pressure. The crude product was purified by preparative reversed phase HPLC.

The coupling of the protected peptide fragment (44.6 mg; 0.08 mmol) with amines (1.1 equiv., 0.088 mmol) was performed with TBTU (1.1 equiv., 0.088 mmol) in DMF with Dipea (2.5 equiv.) as base for 4 hours. In case of example 21 benzyl amine was applied. The solution was evaporated under reduced pressure, dissolved in methanol and again evaporated. The deprotection of the tBu-ester was performed with 90% TFA/water (2 ml) within 2 hours. The solution was evaporated and the residue was treated with saturated aq. LiOH solution (1 ml) and methanol (1 ml) for 1 hour. 95% TFA/water (300 µl) was added and the solution was evaporated under reduced pressure. The crude product was purified by preparative reversed phase HPLC applying an acetonitrile/water gradient. The product gave satisfactory analytical data. ES-MS: m/z=591.8 ([M+H]+)

The examples 8–9, 12–16, 18–19, 21, 23, 26, 28–32, 34–36, and 38 were synthesized analogously.

Example A

Examples of Pharmaceutical Formulations

| a) Tablets | per tablet |
|---|---|
| Active substance (Example 1) | 50 mg |
| Lactose | 170 mg |
| Corn starch | 260 mg |
| Polyvinylpyrrolidone | 15 mg |
| Magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| b) Tablets | per tablet |
|---|---|
| Active substance (Example 1) | 40 mg |
| Corn starch | 210 mg |
| Lactose | 65 mg |
| Microcrystalline cellulose | 40 mg |
| Polyvinylpyrrolidone | 20 mg |
| Sodium-carboxymethyl starch | 23 mg |
| Magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| c) Coated tablets | per coated tablet |
|---|---|
| Active substance (Example 1) | 5 mg |
| Corn starch | 41.5 mg |
| Lactose | 30 mg |
| Polyvinylpyrrolidone | 3 mg |
| Magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| d) Capsules | per capsule |
|---|---|
| Active substance (Example 1) | 25 mg |
| Corn starch | 283.5 mg |
| Magnesium stearate | 1.5 mg |
| | 310 mg |

The substance and corn starch are mixed and moistened with water. The moist mass is screened and dried. The dry granules are screened and mixed with magnesium stearate. The finished mixture is packed into size 1 hard gelatine capsules.

| e) Ampoule solution | |
|---|---|
| Active substance (Example 1) | 0.5 mg |
| Sodium chloride | 50 mg |
| Water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 0,5 mg, 2,5 mg and 5,0 mg of active substance.

| f) Suppositories | |
|---|---|
| Active substance (Example 2) | 30 mg |
| Solid fat | 1670 mg |
| | 1700 mg |

The solid fat is melted. The ground active substance is homogeneously dispersed at 40° C. It is cooled to 38° C. and poured into slightly chilled suppository moulds.

As used herein, the term "treatment" means that the compounds of the invention can be used in humans with at least a tentative diagnosis of disease. The compounds of the invention will delay or slow the progression of the disease thereby giving the individual a more useful life span.

The term "prevention" means that the compounds of the present invention are useful when administered to a patient who has not been diagnosed as possibly having the disease at the time of administration, but who would normally be expected to develop the disease or be at increased risk for the disease. The compounds of the invention will slow the development of disease symptoms, delay the onset of the disease, or prevent the individual from developing the disease at all.

Prevention also includes administration of the compounds of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

The compounds of the invention are administered in a therapeutically effective amount. The therapeutically effective amount will vary depending on the particular compound used and the route of administration, as is known to those skilled in the art.

The compounds of the invention can be administered orally, parenterally, (IV, IM, depo-IM, SQ, and depo SQ), sublingually, intranasally, inhalative, intrathecally, topically, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenteral administration or aerosols for inhalative administration. Typically the compounds described above are formulated into pharmaceutical compositions using techniques and procedures well known in the art.

About 1 to 500 mg of a compound or mixture of compounds of the invention or a physiologically acceptable salt thereof is admixed with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action.

The compounds may be formulated as the sole pharmaceutically active ingredient in the composition or may be combined with one or more different active ingredients.

The concentration of the compound is effective for delivery of an amount upon administration that lessens or ameliorates at least one symptom of the disorder for which the compound is administered. Typically, the compositions are formulated for single dosage administration.

The compounds and compositions of the invention can be enclosed in multiple or single dose containers. The compounds and compositions according to the invention can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials and the like for parenteral administration; and patches, medipads, creams, and the like for topical administration, and optionally pre-filled inhalators for inhalative administration.

The concentration of active compound in the drug composition will depend on absorption, inactivation, and excretion rates of the active compound, the dosage schedule, and amount administered as well as other factors known to those of skill in the art.

It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, lozenges or troches.

Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Methods for preparation of such formulations are known to those skilled in the art.

The oral dosage forms are administered to the patient 1, 2, 3, or 4 times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit beta-secretase activity, to inhibit A beta production, to inhibit A beta deposition, or to treat or prevent AD is from about 0.1 mg/day to about 1,000 mg/day. It is preferred that the oral dosage is from about 1 mg/day to about 100 mg/day. It is more preferred that the oral dosage is from about 5 mg/day to about 50 mg/day. It is understood that while a patient may be started at one dose, that dose may be varied over time as the patient's condition changes.

The invention here is the new compounds of the invention and new methods of using the compounds of the invention. Given a particular compound of the invention and a desired dosage form, one skilled in the art would know how to prepare and administer the appropriate dosage form.

The compounds of the invention are used in the same manner, by the same routes of administration, using the same pharmaceutical dosage forms, and at the same dosing schedule as described above, for preventing disease or treating patients with MCI (mild cognitive impairment) and preventing or delaying the onset of Alzheimer's disease in those who would progress from MCI to AD, for treating or preventing Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type of Alzheimer's disease.

The compounds of the invention can be used in combination, with each other or with other therapeutic agents or approaches used to treat or prevent the conditions listed above. Such agents or approaches include: acetylcholinesterase inhibitors such as tacrine (tetrahydroaminoacridine, marketed as COGNEXO), donepezil hydrochloride, (marketed as Aricept and rivastigmine; gamma-secretase inhibitors; anti-inflammatory agents such as cyclooxygenase II inhibitors; anti-oxidants such as Vitamin E and ginkolides; immunological approaches, such as, for example, immunization with A beta peptide or derivatives thereof or administration of anti-A beta peptide antibodies; neurotransmitter modulators like NS-2330; statins (HMG-CoA Reductase Inhibitors); and direct or indirect neurotropic agents such as Cerebrolysin (AIT-082) (Emilieu, 2000, Arch. Neurol. 57: 454), and other neurotropic agents of the future.

Most preferred are combinations with one or more additional active ingredient selected from the group consisting of atorvastatin, besipirdine, cevimeline, donepezil, eptastigmine, galantamine, glatiramer acetate, icopezil, ipidacrine, lazabemide, linopirdine, lubeluzole, memantine, metrifonate, milameline, nefiracetam, nimodipine, octreotide, rasagiline, rivastigmine, sabcomeline, sabeluzole, tacrine, valproate sodium, velnacrine, YM 796, phenserine and zanapezil and/or with an antiinflammtory agents selected from the group consisting of rofecoxib, celecoxib, valdecoxib, nitroflurbiprofen, IQ-201, NCX-2216, CPI-1189, colostrinin, ibuprofen, indomethacin, meloxicam, R-flurbiprofen and sulindac sulphide and/or one or more additional nerve growth factor and/or nerve growth modulator selected from the group consisting of: ABS-205, Inosine, KP-447, leteprinim, MCC-257, NS-521, NS-521, NS-2330, xaliproden.

It should be apparent to one skilled in the art that the exact dosage and frequency of administration will depend on the particular compounds of the invention administered, the particular condition being treated, the severity of the condition being treated, the age, weight, general physical condition of the particular patient, and other medication the individual may be taking as is well known to administering physicians who are skilled in this art.

The compounds of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). While not wishing to be bound by a particular theory, inhibition of beta-secretase activity is thought to inhibit production of beta amyloid peptide(A beta). Inhibitory activity is demonstrated in one of a variety of inhibition assays, whereby cleavage of an APP substrate in the presence of a beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pat. Nos. 5,942,400, 5,744, 346, as well as in the examples below.

The enzymatic activity of beta-secretase and the production of A beta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, animal models expressing native APP and enzyme, or may utilize transgenic and non-transgenic animal models expressing the substrate and enzyme. Detection of enzymatic activity can be by analysis of one or more of the cleavage products, for example, by immunoassay, fluorometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Various forms of beta-secretase enzyme are known, and are available and useful for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Hussain et. al., 1999, Mol. Cell. Neurosci. 14: 419–427; Vassar et. al., 1999, Science 286: 735–741; Yan et. al., 1999, Nature 402: 533–537; Sinha et. al., 1999, Nature 40: 537–540; and Lin et. al., 2000, PNAS USA 97: 1456–1460). Synthetic forms of the enzyme have also been described (WO98/22597 and WO00/17369). Beta-secretase can be extracted and purified from human brain tissue and can be produced in cells, for example mammalian cells expressing recombinant enzyme.

Determination of BACE Activity In Vitro

Activity of BACE can be analyzed by different assay technologies, all incubating a catalytically active form of BACE with a potential substrate in a suitable buffer. The decrease in substrate concentration or the increase in product concentration can be monitored by applying different techniques depending on the nature of the substrate and include but are not limited to HPLC-MS analysis, fluorescence assays, fluorescence quenching assays. The substrate can be a peptide containing an amino acid sequence which is can be hydrolyzed by BACE which may be conjugated with dyes suitable for the detection system chosen or may extend to the protein substrate. As enzyme source, the full-length BACE enzyme can be used as well as the catalytically active ectodomain of the protein. An alternative assay format based on competition of the test compound with a BACE binding compound can be used.

For $IC_{50}$ determination different concentrations of compound are incubated in the assay. The relative compound inhibition potency is determined by calculating the concentration of compound that showed a 50% reduction in detected signal compared to the enzyme reaction signal in the control wells with no added compound.

Useful inhibitory compounds are effective to inhibit 50% of beta-secretase enzymatic activity at a concentration of less than 50 micro molar, preferably at a concentration of 10 micro molar or less, more preferably 1 micro molar or less, and most preferably 10 nano molar or less.

In order to obtain the in vitro BACE inhibitory profile of the compounds of the invention they can be tested in the assays as outlined in the examples:

Example Bace Assay

For each compound being tested, the BACE activity is monitored in a fluorescence quenching assay using the ectodomain of BACE (aa 1-454) fused to a myc-his tag and secreted from HEK293/APP/$BACE_{ect.}$cells into Opti-MEM™ (Invitrogen) as enzyme source. The substrate peptide used has the amino acid sequence SEVNLDAEFK and possesses a Cy3-fluorophore at the N-terminus and a Cy5Q-quencher (Amersham) at the C-terminus. The substrate is dissolved at 1 mg/ml in DMSO.

The assay is performed in the presence of 10 µl OptiMEM containing the ectodomain of BACE, 100 µl water containing the desired concentration of compound with a max. conc. of 1% DMSO, 1 µM substrate peptide, and 20 mM NaOAc, pH 4.4 in a total assay volume of 200 µl in a 96 well plate. The reaction is incubated at 30° C. in a fluorimeter and the cleavage of the substrate is recorded as kinetic for 30 min. at ex: 530 nm, em: 590 nm. The water used for preparation of the buffer or compound dilution is of highest purity. Blank wells containing either no inhibitor or no enzyme are included on each plate.

The compounds of formula (I) exemplified as examples 1 to 38 show $IC_{50}$ values of less than 30 micro molar.

Aβ Secretion Assay

The secretion of Aβ can be monitored in cell lines of different origin. A representative set of such cells include but are not limited to human embryonic kidney 293 cells (HEK293), Chinese hamster ovary cells (CHO), human H4 neuroglimoa cells, human U373-MG astrocytoma glioblastoma cells, murine neuroblastoma N2a cells which are stably or transiently transfected with APP or mutated forms of APP which include but is not limited to the Swedish or London/ Indiana mutations. Transfection of the cells can for example be achieved by introducing a pcDNA3 plasmid (Invitrogen) containing the human APP cDNA of interest using a transfection reagent like Lipofectamine (Invitrogen) according to the instructions of the manufacturer.

Secretion of Aβ can also on a routine basis be analyzed from cells producing without genetic modification sufficient amounts of Aβ or by using highly sensitive Aβ detection assays. Cells suitable for an analysis of this kind include but are not limited to human IMR-32 neuroblastoma cells.

Secretion of Aβ from cells can also me analyzed from brain derived cells obtained from embryos or the new born offspring from APP transgenic mice as of example the mice described by Hsiao et al (Hsiao et al 1996 Science 274: 99–102). In addition brain derived cells from other organism such as rat or guinea pig may also be used.

Useful inhibitory compounds are effective to inhibit 50% of beta-secretase enzymatic activity in these cellular assays at a concentration of less than 50 micro molar, preferably at a concentration of 10 micro molar or less, more preferably 1 micro molar or less, and most preferably 10 nano molar or less.

Example Aβ Secretion Assay

In the following a protocol for the determination of Aβ from U373-MG cells which are stably expressing $APP_{751}$ under the control of a CMV promoter is given. The cells can be maintained in a culture medium like DMEM+glucose, sodium pyruvate, glutamine, pyridoxine-HCl, and 10% FCS. The cells are kept in an incubator at 37° C. in a water saturated atmosphere of 5% $CO_2$. For assaying compounds a confluent cell layer is incubated with compound concentrations in the range of 50 µM to 50 pM, originally dissolved in DMSO and for the assay diluted in 150 µl of the medium described, for 12–24 hours. The production of Aβ during this period of time in the presence or absence of compound is monitored by sandwich ELISA specific for Aβ40 and Aβ42. The antibodies 6E10 (Senetek) and SGY3160 (C. Eckman, Mayo Clinic, Jacksonville, Fla.) are used as capture antibodies and immobilized to the plate. Unspecific protein binding is blocked with Block Ace (Serotec) before adding the Aβ containing cell culture supernatant. The detection antibodies specific for Aβ40 and Aβ42 (Nanotools, Germany) are conjugated with alkaline phosphatase which activity is quantified using the substrate CSPD/Sapphire II (Applied Biosystems) according to the manufacturers instructions.

Potential effects of the compound in altering the Aβ level induced by an unspecific toxicity related mechanism are addressed by the reduction of AlamarBlue (Resazurin) after 60 min. Potency of non-toxic compounds is determined by calculating the concentration of compound that showed a 50% reduction in the detected signal compared to the cells in the control wells with no added compound.

The compounds of formula (I) exemplified as examples 1 to 38 show an inhibitory effect in the Aβ secretion essay.

Various animal models can be used to analyze beta-secretase activity and/or processing of APP to release A beta, as described above. For example, transgenic animals expressing APP substrate and beta-secretase enzyme can be used to demonstrate inhibitory activity of the compounds of the invention. Certain transgenic animal models have been described, for example, in U.S. Pat. Nos. 5,877,399; 5,612,486; 5,387,742; 5,720,936; 5,850,003; 5,877,015 "and U.S. Pat. No. 5,811,633, and in Games et. al., 1995, Nature 373: 523. Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

What is claimed is:

1. A compound of formula (I)

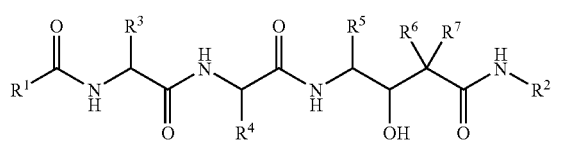

(I)

wherein
R$^1$ represents
 a) a carboxy-C$_{1-6}$-alkyl-,
 b) a C$_{1-6}$-alkyl-O—CO—C$_{1-6}$-alkyl-,
 c) a C$_{3-8}$-cycloalkyl- or C$_{3-8}$-cycloalkyl-C$_{1-3}$-alkyl-,
 d) a heterocyclyl-,
 e) a aryl-, or a aryl-C$_{1-3}$-alkyl-, or
 f) a heteroaryl-group
  wherein each of said groups may be optionally substituted by one or more substituents independently selected from the group consisting of C$_{1-6}$-alkyl-, aryl-CO—, C$_{1-6}$-alkyl-O—, C$_{1-6}$-alkyl-O—CO—, C$_{1-6}$-alkyl-CO—, C$_{1-6}$-alkyl-CO—NR$^8$—, halogen-, carboxy-, hydroxy-, nitro-, oxo- or (R$^8$)$_2$N—SO$_2$-groups,
R$^2$ represents
 (a) a C$_{1-6}$-alkyl- or C$_{2-6}$-alkenyl-group,
  optionally substituted by one or more substituents independently selected from the group consisting of heteroaryl-, phenyl-, C$_{3-8}$-cycloalkyl- or heterocyclyl-groups,
   wherein the phenyl group may be optionally substituted by one or more substituents independently selected from the group consisting of C$_{1-3}$-alkyl-groups which may be optionally substituted with a hydroxyl-group, cyano-, C$_{1-3}$-alkynyl-, halogen, hydroxy-, carboxy-, nitro-, (R$^8$)$_2$N—CO—, (R$^8$)$_2$N— or C$_{1-3}$-alkyl-N(R$^8$)C(O)N(R$^8$)-groups, or
 (b) a bicyclic carbocyclic ring,
  optionally substituted by one or more substituents independently selected from the group consisting of C$_{1-3}$-alkyl-, halogen, hydroxy-, carboxy-, nitro-, (R$^8$)$_2$N—CO— or (R$^8$)$_2$N-groups,
R$^3$ represents a C$_{1-6}$-alkyl-, C$_{1-6}$-alkylthio-C$_{1-3}$-alkyl-, C$_{2-6}$-alkenyl, C$_{2-6}$-alkinyl or a C$_{3-8}$-cycloalkyl-C$_{1-3}$-alkyl-group,
 optionally substituted by one or more substituents independently selected from the group consisting of fluor or cyano-,
R$^4$ represents a C$_{1-6}$-alkyl-, C$_{2-6}$-alkenyl-, C$_{3-8}$-cycloalkyl-C$_{1-3}$-alkyl-, aryl-, aryl-C$_{1-3}$-alkyl- or a heteroaryl-C$_{1-3}$-alkyl-group,
 wherein each of said groups may be optionally substituted by one or more substituents independently selected from the group consisting of C$_{1-6}$-alkyl-, C$_{1-6}$-alkyl-O—, (R$^8$)$_2$N—CO—, aryl-C$_{1-3}$-alkyl-O— or hydroxy-groups,
R$^5$ represents a C$_{1-6}$-alkyl-, C$_{3-8}$-cycloalkyl-C$_{1-3}$-alkyl- or a aryl-C$_{1-3}$-alkyl-group,
 wherein each of said groups may be optionally substituted by one or more substituents independently selected from C$_{1-6}$-alkyl-S— or a halogen atom,
R$^6$ and R$^7$ each independently represent hydrogen or a halogen atom,
R$^8$ represents hydrogen or a C$_{1-6}$-alkyl-group,
or a pharmaceutically acceptable salt or solvate thereof.

2. The compound according to claim 1, wherein R$^1$ represents a group selected from a 3-carboxypropyl-, 3-methoxycarbonylpropyl-, 1-methyl-cyclohexyl, 1-acetylpiperidin-3-yl-, 1-benzoylpiperidin-3-yl-, phenyl-, 3-carboxyphenyl-, 3-hydroxyphenyl-, 4-hydroxyphenyl-, 2-fluoro-4-hydroxyphenyl-, 3-fluoro-4-hydroxyphenyl-, 3-chloro-4-hydroxyphenyl-, 3,5-dichloro-4-hydroxyphenyl-, 3-acetylaminophenyl-, 3-acetylphenyl-, 4-methoxyphenyl-, 3-nitrophenyl-, 4-nitrophenyl-, 3-nitro-4-hydroxyphenyl-, 4-methoxycarbonylphenyl-, 3-methoxycarbonylphenyl-, 4-hydroxy-2,3,5,6-tetrafluorophenyl-, 4-sulfamoylphenyl-, 3-hydroxybenzyl-, 4-hydroxybenzyl-, 1-(4-hydroxyphenyl)-2-methylpropyl-, 5-hydroxypyrazin-2-yl-, 6-hydroxypyridin-3-yl-, 6-oxo-1,6-dihydropyridazin-3-yl-, pyridin-2-yl-, pyridin-3-yl-, pyridin-4-yl-, pyridin-2-yl N-oxide, pyridin-3-yl N-oxide or a pyridin-4-yl N-oxide group.

3. The compound according to claim 1, wherein R$^1$ represents a group selected from a 3-carboxypropyl-, pyridin-2-yl N-oxide, pyridin-3-yl N-oxide, pyridin-4-yl N-oxide or a phenyl-group, wherein the phenyl group is substituted by one or more substituents independently selected from the group consisting of hydroxy groups, carboxy groups or halogen atoms.

4. The compound according to claim 1, wherein
$R^1$ represents a group selected from a 3-carboxypropyl-, pyridin-4-yl N-oxide, 3-carboxyphenyl- or a 4-hydroxy-2,3,5,6-tetrafluorophenyl-group.

5. The compound according to claim 1, wherein
$R^1$ represents a group selected from a 3-carboxypropyl- or a pyridin-4-yl N-oxide-group.

6. The compound according to claim 1, wherein
$R^2$ represents
  (a) a $C_4$-alkyl- or $C_{2-5}$-alkenyl-group,
    optionally substituted by one or more substituents independently selected from the group consisting of pyridinyl-, thienyl-, phenyl- or cyclohexyl-groups,
      wherein the phenyl group may be optionally substituted by one or more substituents independently selected from the group consisting of hydroxymethyl-, cyano-, halogen, hydroxy-, carboxy-, nitro-, $H_2N$—CO—, $H_2N$— or Me-NH—CO—NH-groups, or
  (b) a bicyclic carbocyclic ring,
    optionally substituted by one or more substituents independently selected from the group consisting of $C_{1-3}$-alkyl-, halogen, hydroxy-, carboxy-, nitro-, $H_2N$—CO— or $H_2N$-groups.

7. The compound according to claim 1, wherein
$R^2$ represents an ethyl-group,
  or a substituent selected from the group consisting of

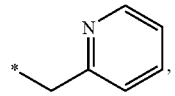 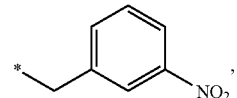

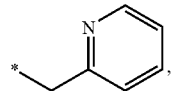 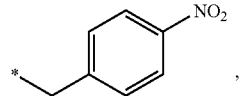

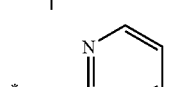 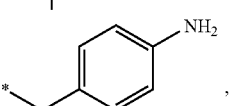

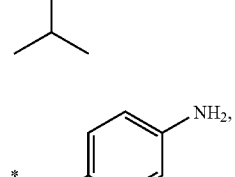 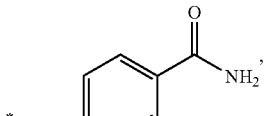

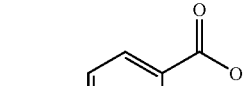 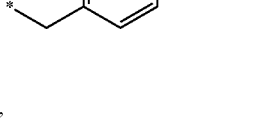

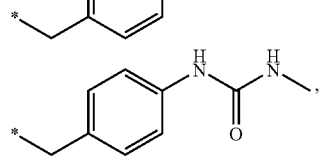

-continued

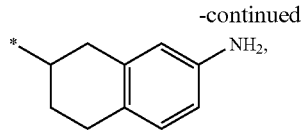

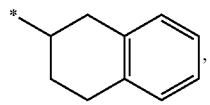

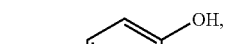

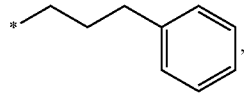

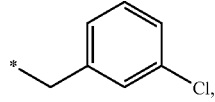

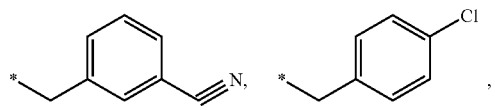

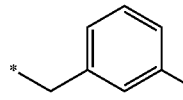 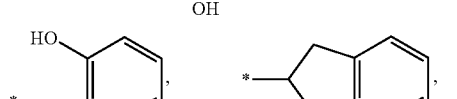

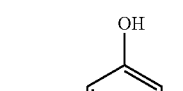 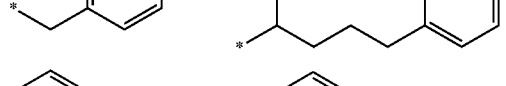

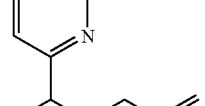 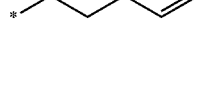

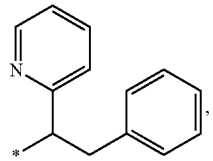

-continued

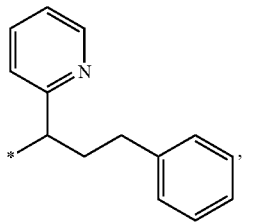

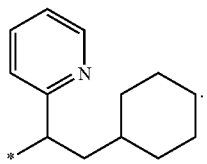

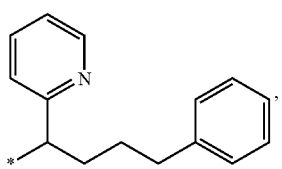

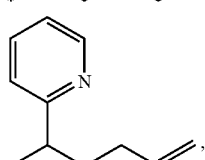

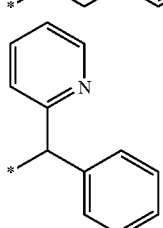

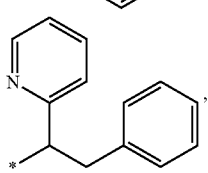

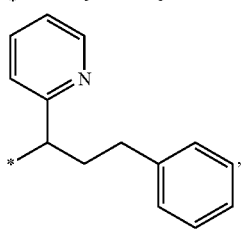

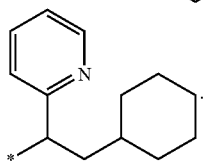

8. The compound according to claim 1, wherein
$R^3$ represents a n-propyl-, 2-methylpropyl-, 2,2-dimethylpropyl-, 1-methylpropyl-, 3-methylbutyl-, ethyl-, or a cyclopropylmethyl-group.

9. The compound according to claim 1, wherein
$R^3$ represents a 1-methylpropyl- or a 2,2-dimethylpropyl-group.

10. The compound according to claim 1, wherein
$R^4$ represents a methyl-, n-propyl-, 1-methylpropyl-, methoxymethyl-, prop-2-enyl-, cyclopropylmethyl-, aminocarbonylmethyl-, phenyl-, 2-phenylethyl-, 3-phenylpropyl-, 2-(4-hydroxyphenyl)ethyl-, 2-(4-methoxyphenyl)ethyl-, benzyloxymethyl or a indol-3-ylmethyl-group.

11. The compound according to claim 1, wherein
$R^4$ represents a n-propyl-, prop-2-enyl- or a cyclopropylmethyl-group.

12. The compound according to claim 1, wherein
$R^5$ represents a n-propyl-, 2-methylpropyl-, n-butyl-, methylthioethyl-, cyclohexylmethyl-, benzyl- or a 3,5-difluorbenzyl-group.

13. The compound according to claim 1, wherein
$R^5$ represents a 2-methylpropyl- or a 3,5-difluorbenzyl-group.

14. A compound selected from the following examples (1) through (38)

(1)

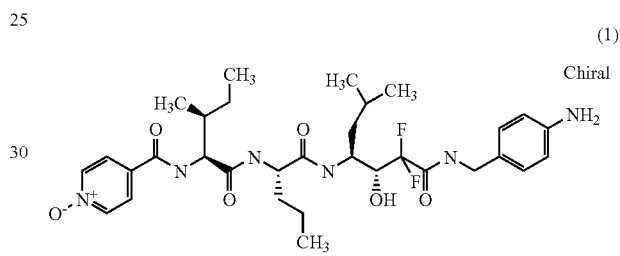

(2)

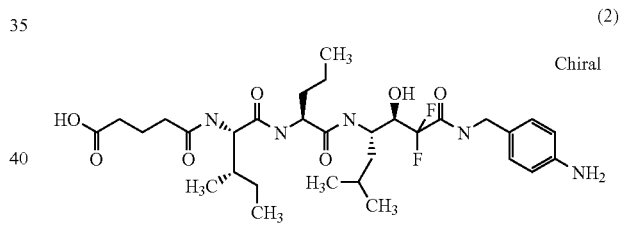

(3)

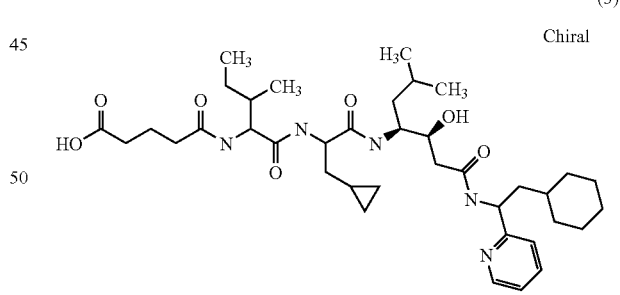

(4)

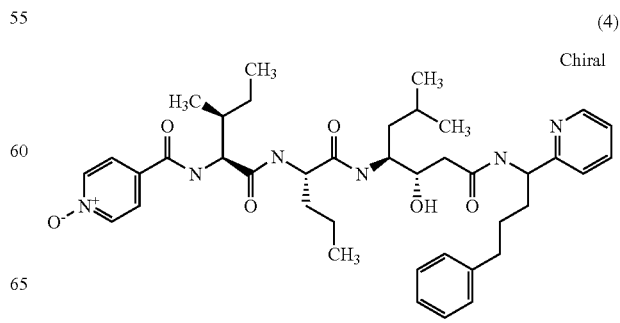

-continued
(5)
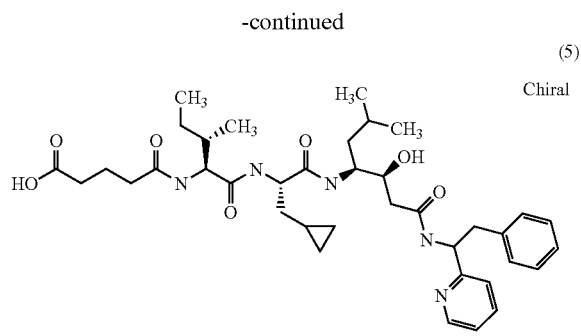
(6)
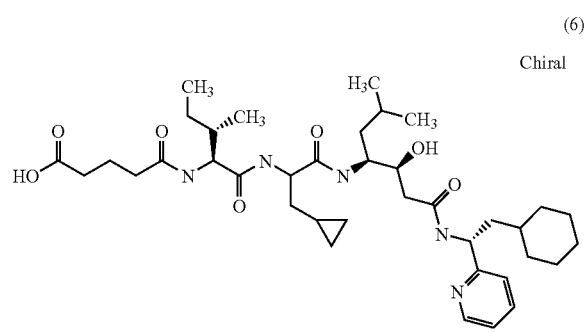
(7)
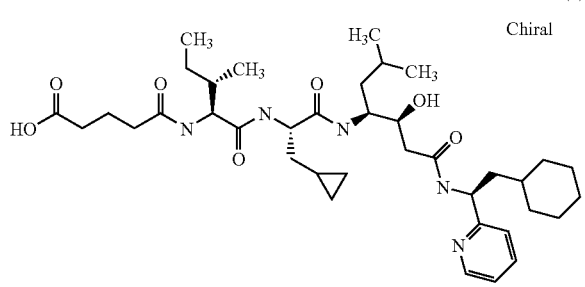
(8)
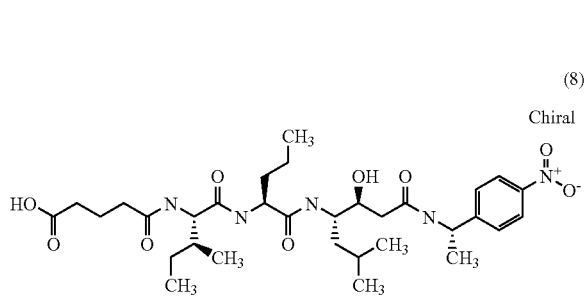
(9)
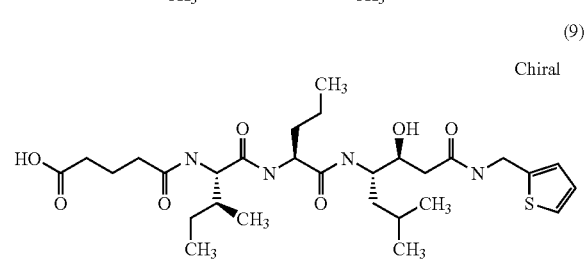
-continued
(10)
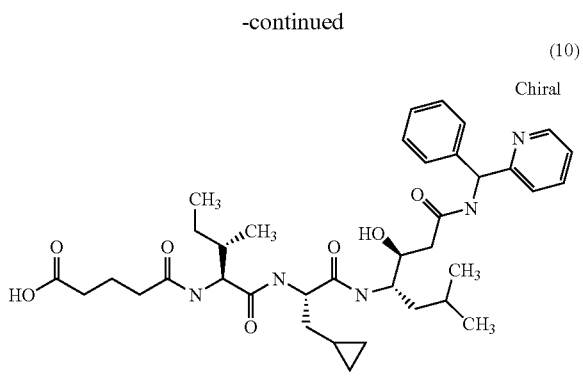
(11)
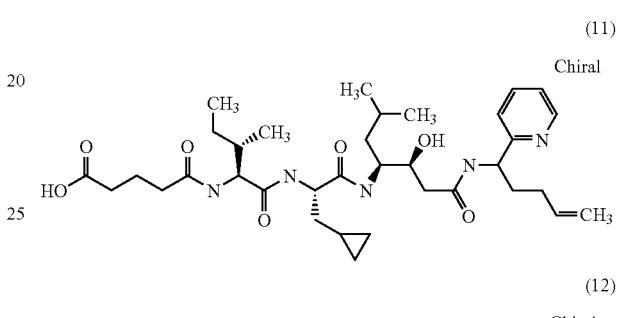
(12)
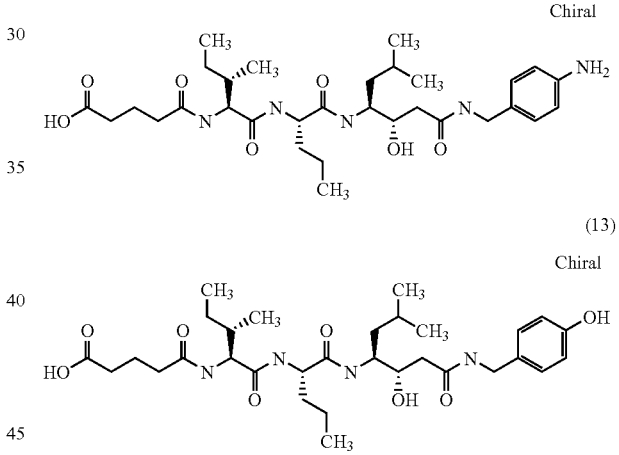
(13)
(14)
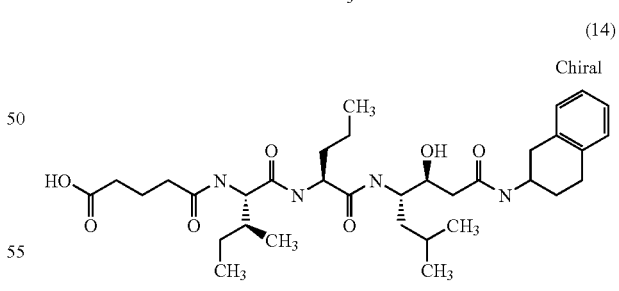
(15)
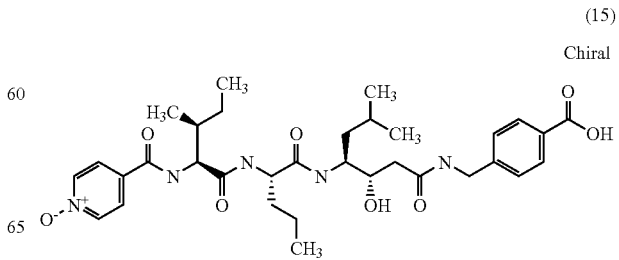

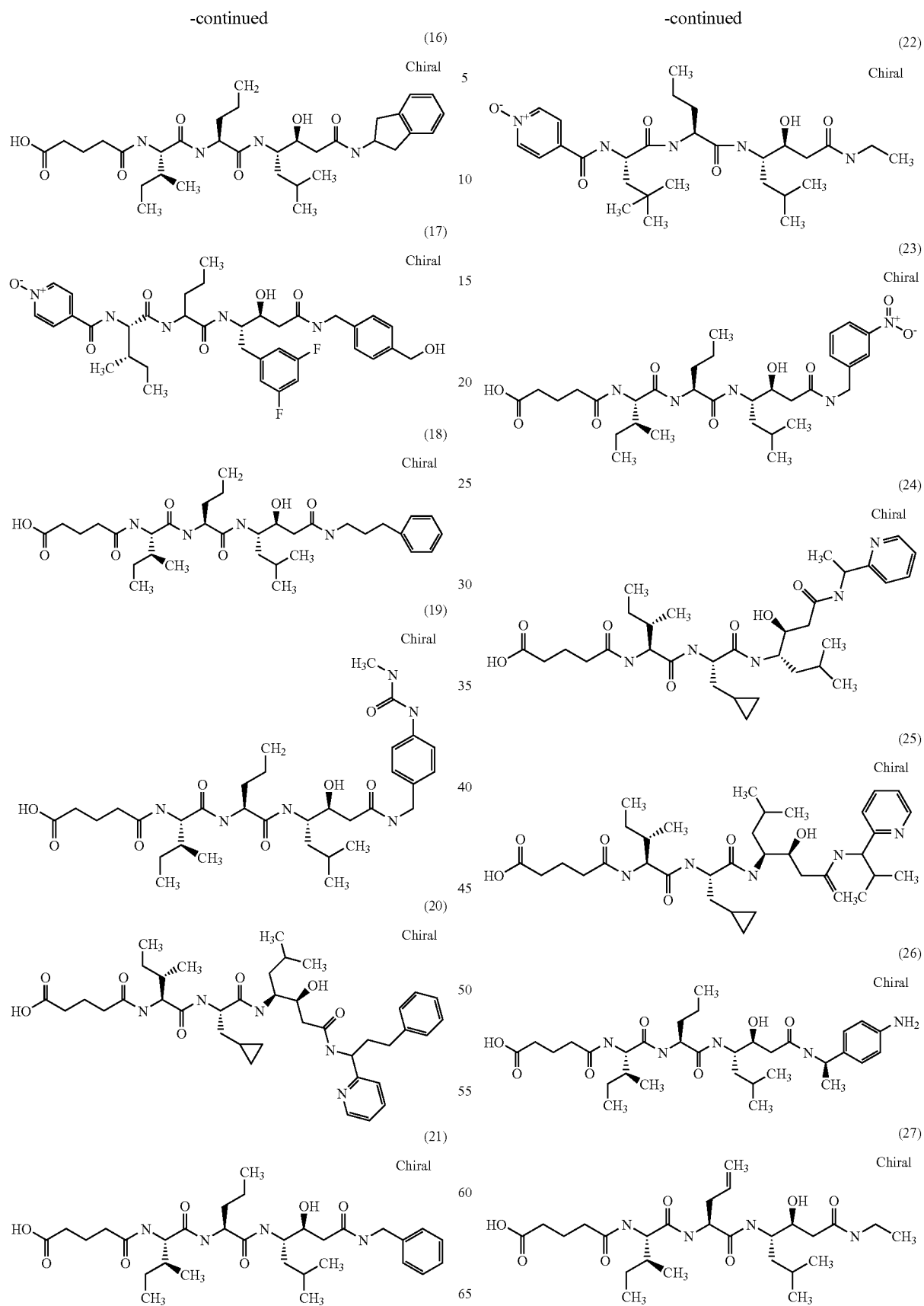

(28)
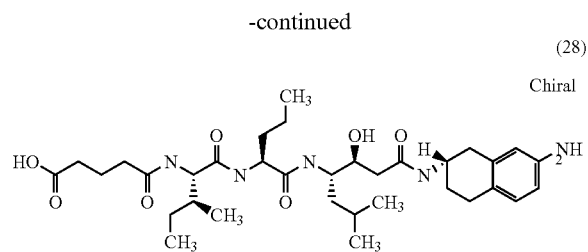
(29)
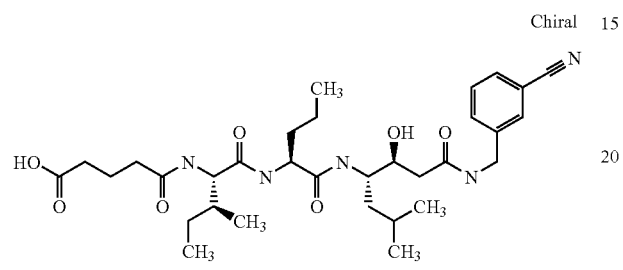
(30)
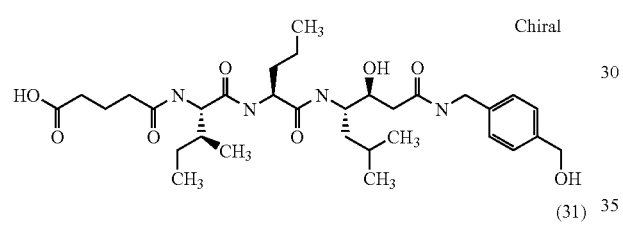
(31)
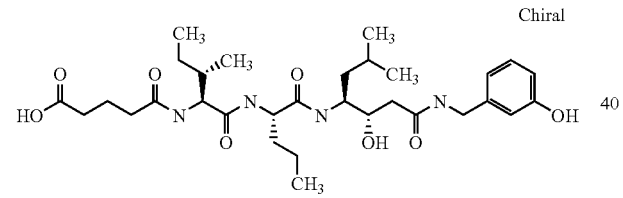
(32)
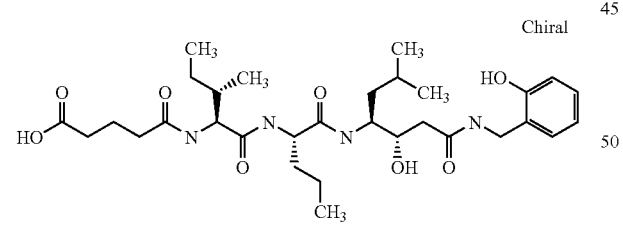
(33)
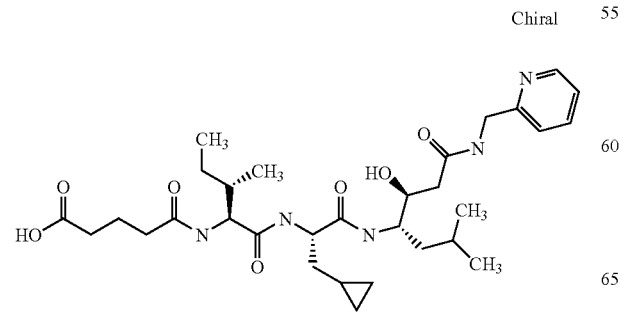
(34)
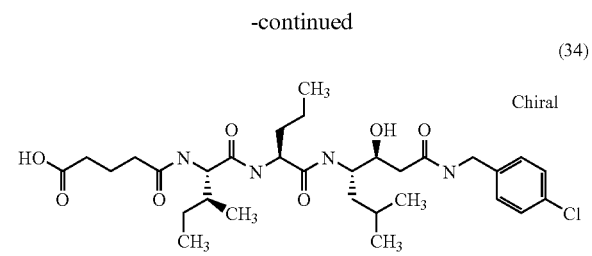
(35)
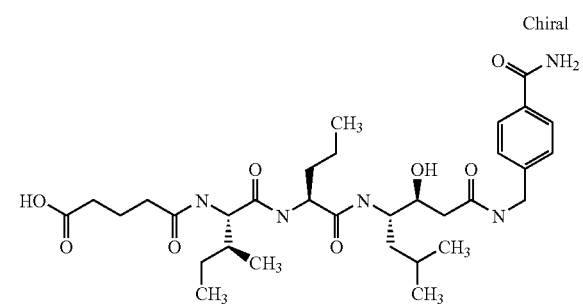
(36)
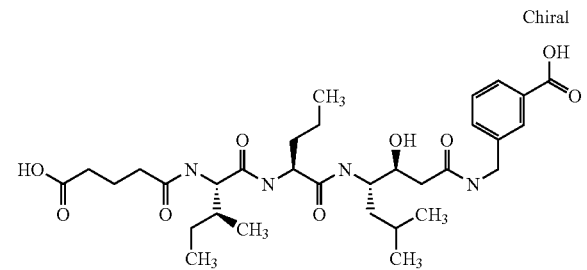
(37)
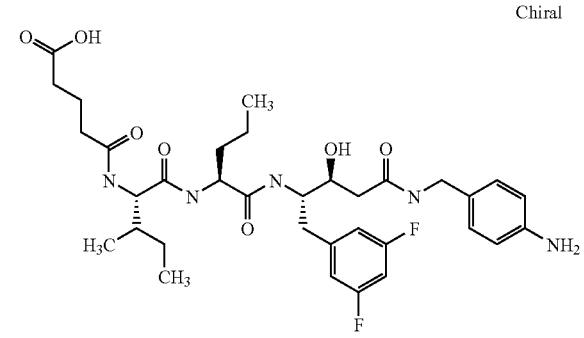
and
(38)
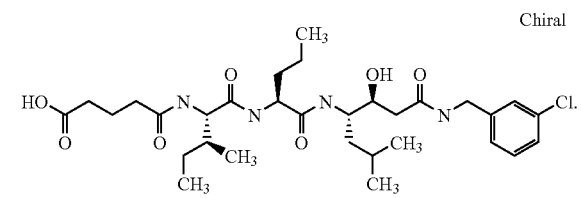
15. A composition comprising a compound according to claim 1 together with a pharmaceutically acceptable carrier or diluent.

16. The pharmaceutical composition according to claim 15, which comprises one or more additional active ingredient selected from the group consisting of atorvastatin, besipirdine, cevimeline, donepezil, eptastigmine, galantamine, glatiramer acetate, icopezil, ipidacrine, lazabemide, linopirdine, lubeluzole, memantine, metrifonate, milameline, nefiracetam, nimodipine, octreotide, rasagiline, rivastigmine, sabcomeline, sabeluzole, tacrine, valproate sodium, velnacrine, YM 796, phenserine and zanapezil.

17. The composition according to claim 15, which comprises one or more additional active ingredient which are antiinflammtory agents selected from the group consisting of rofecoxib, celecoxib, valdecoxib, nitroflurbiprofen, NCX-2216, CPI-1189, colostrinin, ibuprofen, indomethacin, meloxicam, sulindac sulphide, and R-flurbiprofen.

18. The composition according to claim 15, which comprises one or more additional nerve growth factor and/or nerve growth modulator selected from the group consisting of: Inosine, leteprinim, NS-521, and xaliproden.

* * * * *